US012618575B2

(12) United States Patent
Richelieu

(10) Patent No.: US 12,618,575 B2
(45) Date of Patent: May 5, 2026

(54) HVAC UVC LED PROJECTION UNIT FOR HVAC DEVICES

(71) Applicant: UVC Science, Inc., Reno, NV (US)

(72) Inventor: Jozef Richelieu, Reno, NV (US)

(73) Assignee: UVC Science, Inc., Reno, NV (US)

( * ) Notice: Subject to any disclaimer, the term of this patent is extended or adjusted under 35 U.S.C. 154(b) by 343 days.

(21) Appl. No.: 18/319,097

(22) Filed: May 17, 2023

(65) Prior Publication Data

US 2024/0053035 A1    Feb. 15, 2024

Related U.S. Application Data

(60) Provisional application No. 63/343,271, filed on May 18, 2022, provisional application No. 63/442,706, filed on Feb. 1, 2023, provisional application No. 63/483,293, filed on Feb. 5, 2023.

(51) Int. Cl.
*F24F 8/22*          (2021.01)
*A61L 9/20*          (2006.01)

(52) U.S. Cl.
CPC    *F24F 8/22* (2021.01); *A61L 9/20* (2013.01);
*A61L 2209/12* (2013.01); *A61L 2209/15*
(2013.01); *A61L 2209/16* (2013.01)

(58) Field of Classification Search
None
See application file for complete search history.

(56) References Cited

U.S. PATENT DOCUMENTS

| | | | | |
|---|---|---|---|---|
| 6,589,486 B1* | 7/2003 | Spanton | | F24F 11/30 |
| | | | | 422/120 |
| 2010/0041538 A1* | 2/2010 | Arai | | C03C 3/06 |
| | | | | 65/33.1 |
| 2014/0252249 A1* | 9/2014 | Doros | | F21V 14/06 |
| | | | | 362/311.1 |
| 2018/0356109 A1* | 12/2018 | Nomura | | H10H 20/856 |
| 2022/0023482 A1* | 1/2022 | Skelton | | A61L 9/20 |

FOREIGN PATENT DOCUMENTS

| | | | | |
|---|---|---|---|---|
| CN | 212408884 U | * | 1/2021 | |
| CN | 213178680 | | 5/2021 | |
| CN | 213178680 U | * | 5/2021 | |

OTHER PUBLICATIONS

International Search Report and Written Opinion; PCT/US2023/067126; dated Aug. 31, 2023.

* cited by examiner

*Primary Examiner* — Andrew Smyth
(74) *Attorney, Agent, or Firm* — Knobbe, Martens, Olson & Bear, LLP

(57) ABSTRACT
An HVAC UVC light projection unit for providing UVC illumination within an air duct includes at least one UVC light source comprising a UVC LED and a lens configured to receive UVC light from the UVC LED. The UVC light projection unit further comprises a mounting platform for securing to the outside of the duct. An elongate support configured to support the at least one UVC light source connects the mounting platform with the UVC light source via a hole in the wall of the duct such that the UVC light source is inside the duct. The UVC light source is oriented toward the longitudinal direction of the air duct to direct UVC light along the length of the duct.

17 Claims, 15 Drawing Sheets

Aspheric lens allowing 220-290nm UV transmission

UVC Radiance created by high power UV LED diodes collimated in center lens to allow forward projection

28

12c

12b

12a

30

68

10

Radial heatsinks to providing efficient cooling for UV LED diodes

HVAC UVC LED PROJECTION UNIT FOR HVAC DEVICES

RELATED APPLICATIONS

This application claims priority benefit of U.S. Provisional Application No. 63/343,271, filed May 18, 2022, titled "HVAC UV LED PROJECTION MODULE FOR HVAC DUCTING, U.S. Provisional Application No. 63/442,706, filed Feb. 1, 2023, titled "HVAC UVC LED PROJECTION UNIT FOR HVAC DEVICES" and U.S. Provisional Application No. 63/483,293, filed Feb. 5, 2023, titled "HVAC UVC LED PROJECTION UNIT FOR HVAC DEVICES." The entire contents of each of the applications listed in this paragraph are hereby incorporated herein by reference.

TECHNICAL FIELD

The present application generally relates to apparatus or systems for projecting ultraviolet light, and in particular ultraviolet light projection units providing UVC illumination, for example, for sterilization and/or inactivation of air in HVAC (Heat Ventilation and Air Conditioning systems and/or components.

BACKGROUND

The need for sterilization and inactivation of viruses was apparent during the recent COVID pandemic. However, applications involving sterilization and inactivation extend beyond this context. More generally tools that provide the ability to combat airborne infectious viruses and disease carrying bacteria is certainly desirable.

SUMMARY OF THE INVENTION

Various designs described herein may potentially provide for reducing the activity of viruses and/or bacteria in air within HVAC (Heat Ventilation Air Conditioning) systems and/or equipment. In various such designs, UVC light is projected inside an HVAC device such as an air duct or a plenum device (e.g., plenum).

One example design comprises an HVAC UVC light projection unit for providing UVC illumination within an HVAC device (e.g., duct, plenum, plenum chamber, plenum device, etc.). The HVAC device has an inside and an outside and a width in a transverse direction. The HVAC device extends along a longitudinal direction to flow air inside the HVAC device along or opposite to the longitudinal direction. The HVAC UVC light projection unit comprises a mounting platform configured to mount on the outside of the HVAC device. The HVAC UVC light projection unit further comprises an elongate support extending transversely from the mounting platform such that when the mounting platform is mounted on the outside of the HVAC device (e.g., duct, etc.), at least a portion of the elongate support is within the HVAC device. (In some cases, a portion of the elongate support or a portion of the mounting platform extends into or through a hole in the HVAC device, e.g., duct etc., such that the at least one UVC light source is positioned inside the HVAC device, e.g., duct, etc.) The HVAC UVC light projection unit further comprises at least one UVC light source supported on the elongate support. The at least one UVC light source comprises a UVC light emitting diode (LED) configured to emit light having a wavelength and/or a peak wavelength in the range of 260 to 280 nm and a respective lens transmissive to UVC light. The lens is disposed to receive UVC light from said UVC LED and to transmit UVC light such that said light is directed into said HVAC device (e.g., duct, etc.). The UVC light source is configured to be oriented so as to direct UVC light along the longitudinal direction of the HVAC device (e.g., duct, etc.). Other designs and implementations are possible.

BRIEF DESCRIPTION OF THE DRAWINGS

FIG. 1 shows the UVC light source including a plurality of radially directed fins for providing heat dissipation.

FIG. 6 additionally shows a power supply electrically connected to electronics inside the housing of the mounting platform.

FIG. 7 shows the UVC light source supported by the elongate support extending from the mounting platform via a hole in the duct. As illustrated, the UVC light source is oriented so as to point along the length of the inside of duct such that UVC light (e.g., most the UVC light) is directed along the length of the duct.

Figure 11:
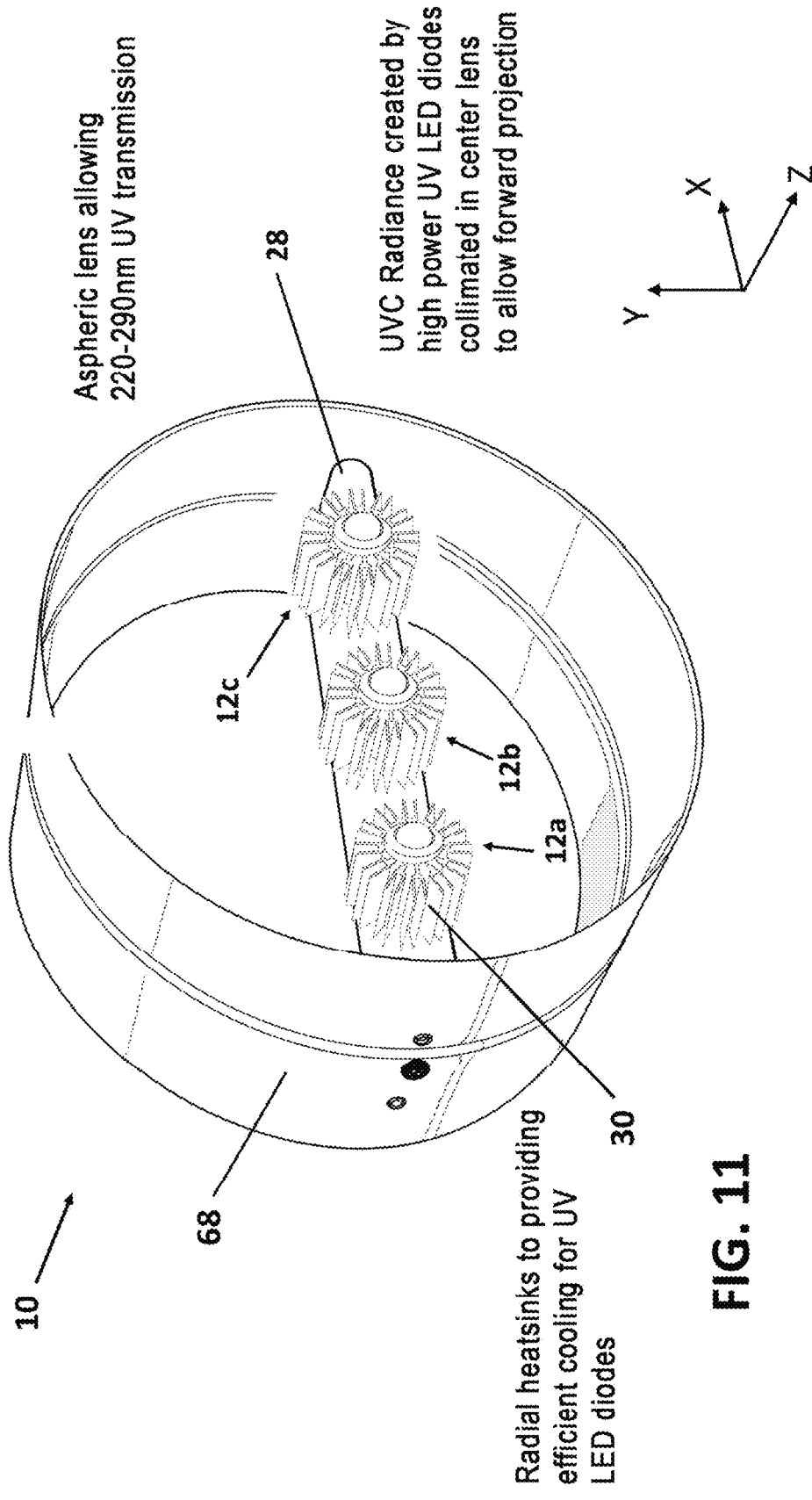

The FIG. 11 shows another design comprising a plurality of UVC light sources supported on an elongate support or arm supported by a frame having a circular shape to fit within an HVAC device such as an air duct having a circular cross-section.

Figure 5:
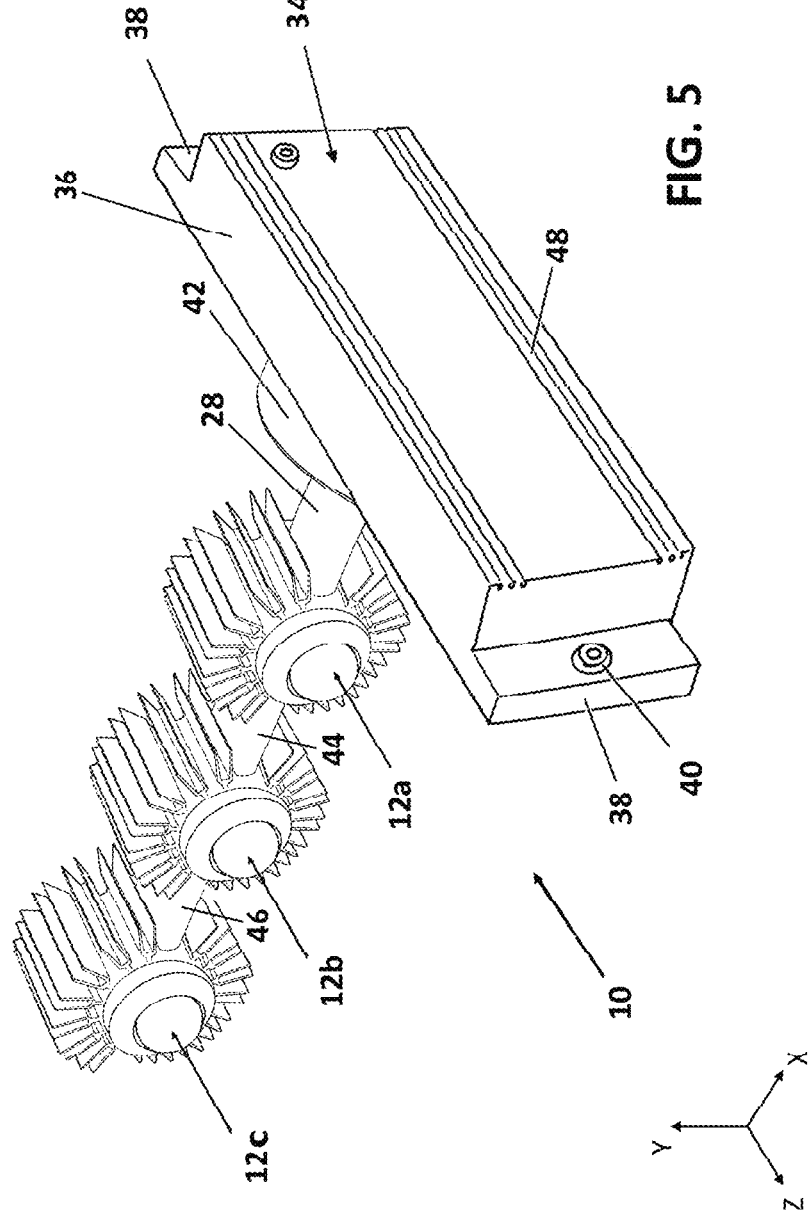
FIG. 5 is a perspective view of HVAC UVC light projection unit for providing UVC illumination within an HVAC device such as an air duct or plenum device (e.g., plenum) similar to that shown in FIGS. 3 and 4 with three, and only three, UVC light sources.
Figure 12A:
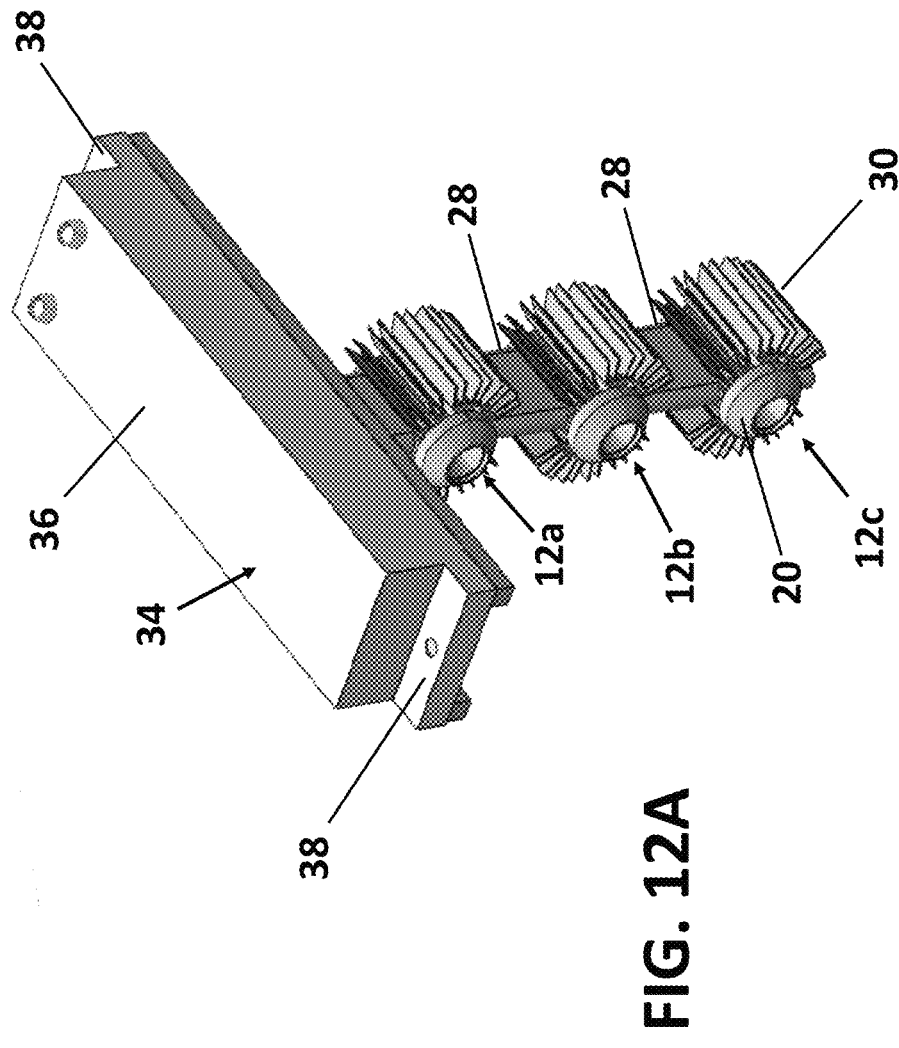

FIG. 12A is a perspective view of a UVC light projection unit, similar to that shown in FIG. 5, having three light sources.

Figure 12B:
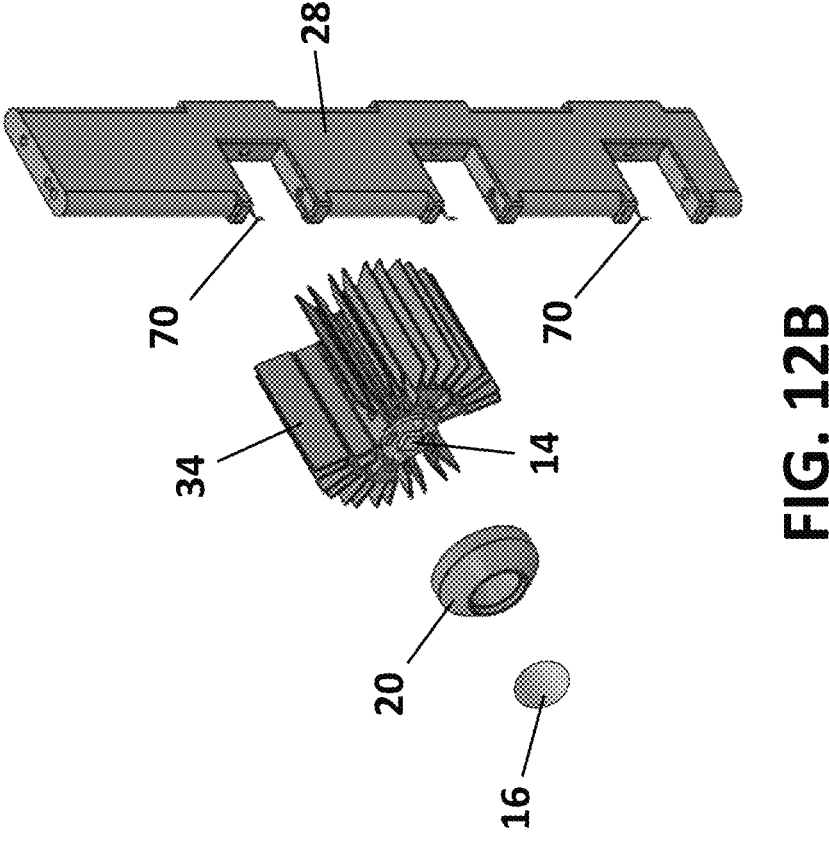

FIG. 12B is an exploded perspective view of the UVC light projection unit, of FIG. 12A, having a single elongate support or arm supporting the plurality (e.g., 3) light sources.

Figure 12C:
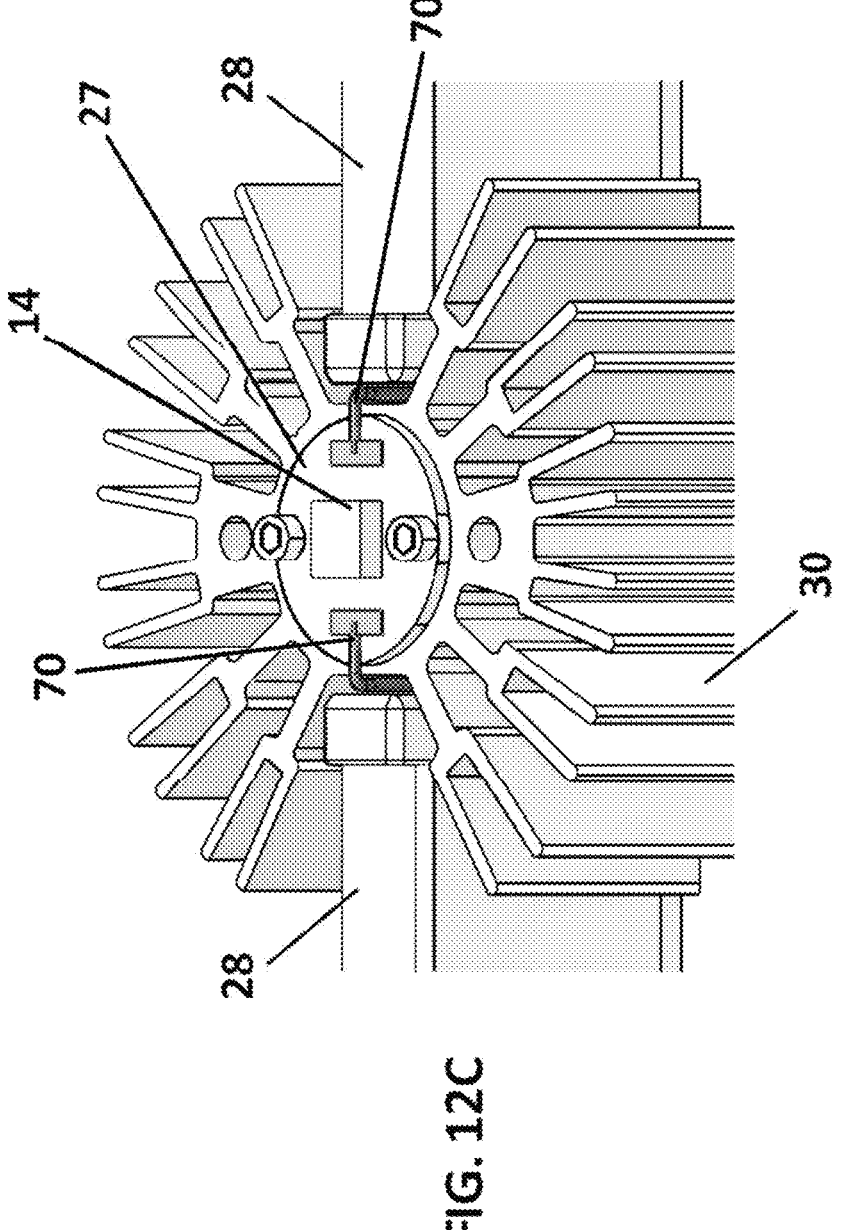

FIG. 12C is a perspective view one of the UVC light sources in the design of FIGS. 12A and 12B showing the UVC LED electrically connected to wires that may be supported by the elongate support or arm.

Figure 12D:
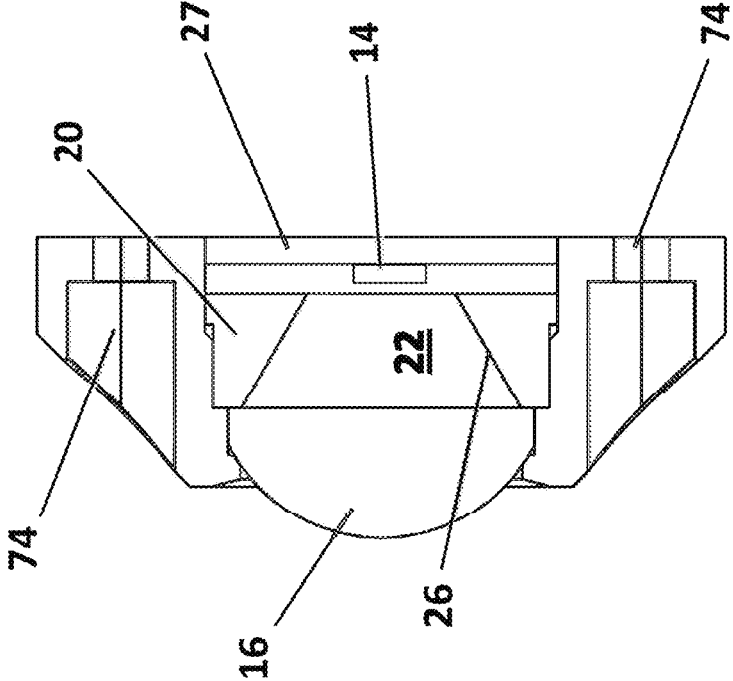

FIG. 12D is a cross-sectional view of the optics mount and lens for one of the UVC light sources in the design of FIG. 12A-12C showing the UVC LED and a channel through which UVC light passes from the UVC LED to the lens.

DETAILED DESCRIPTION

Ultraviolet (UV) light includes wavelengths from 100 nm to 400 nm. This range is often partitioned into subranges such as UV-A, which may be considered to span 315 nm to 400 nm, UV-B, which may be considered to be from 280 nm to 315 nm in wavelength, and UV-C (or UVC as used herein), which may be considered to be from 200 nm to 280 nm.

UVC light can be used to kills or degrades the potency of various harmful microorganisms that may be in the air within air ducts. UVC light attacks nucleic acids and damages the DNA of the microorganism. Accordingly, technology described herein, may be used to partially or fully sterilize or render inactive viruses and/or bacteria along a length of 10 feet within HVAC device such as an air duct or plenum device (e.g., plenum) as the air flows by.

Figure 1:
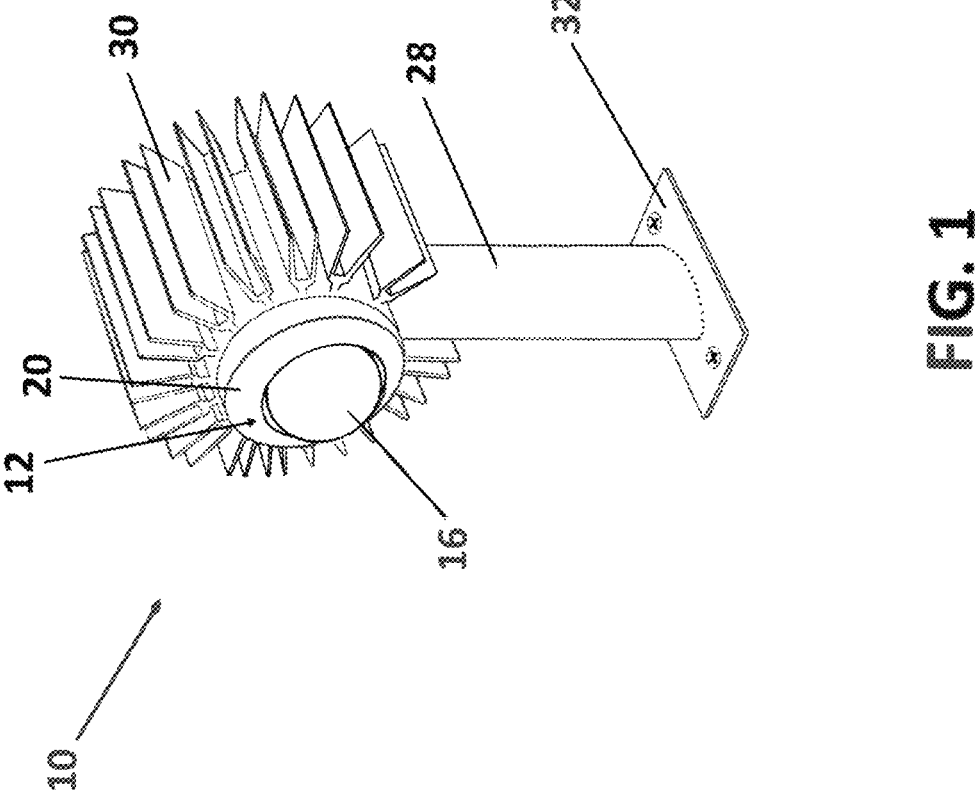
FIG. 1 illustrates a UVC light source on an elongate support for positioning inside an HVAC device such as an air duct or plenum device (e.g., plenum). The UVC light source comprises a UVC light emitting diode (LED) (not shown) inside and/or behind a lens holder or lens retainer with an angled cavity that collects and directs the light rays to a lens.
Figure 2:
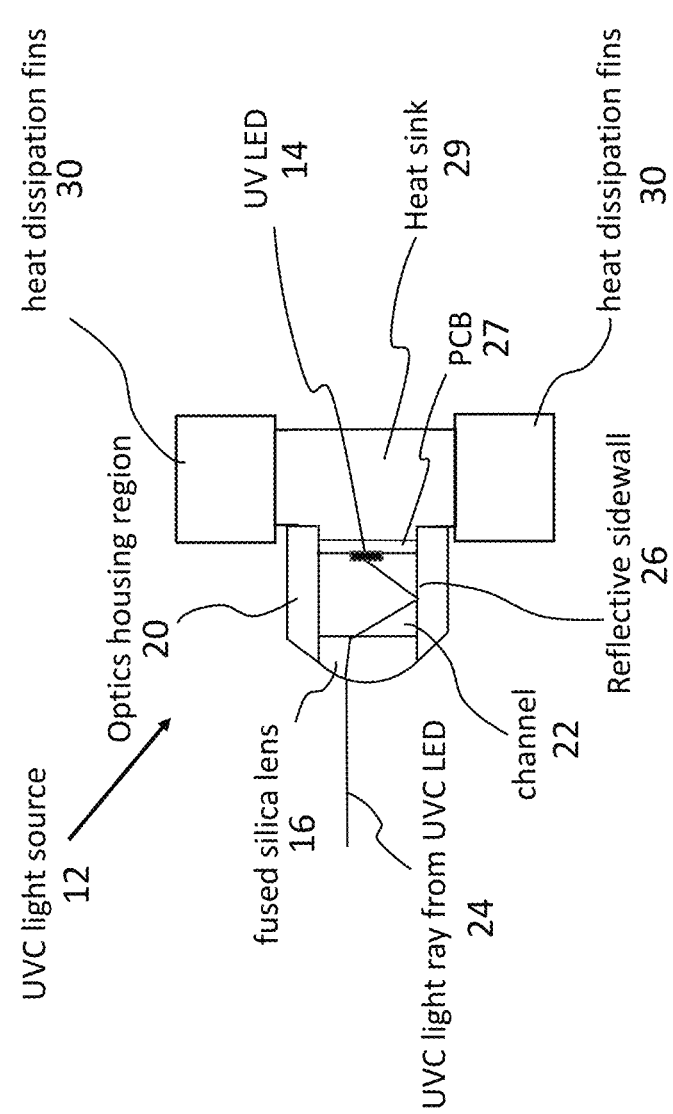
FIG. 2 is a schematic cross-section of a UVC light source such as shown in FIG. 1 for providing UVC illumination within an HVAC device such as an air duct or plenum device (e.g., plenum). As illustrated, the UVC light source comprises a UVC light emitting diode (LED) and a lens transmissive to UVC light. The lens is disposed to receive UVC light from the UVC LED and project the UVC light into the HVAC device generally along the longitudinal direction of the HVAC device.

FIGS. 1 and 2 shows part of a UVC light projection unit 10 for use in introducing UVC light into an HVAC device such as an air duct or plenum device (e.g., plenum). FIG. 1 is a perspective view and FIG. 2 is a schematic cross-sectional view. The HVAC based UVC light projection unit 10 comprises a UVC light source 12 configured to be inserted into HVAC device such, as for example, an air duct or plenum to provide UVC light thereto. In the example shown, the UVC light source 12 comprises a UVC LED 14 (see FIG. 2). The UVC light source 12 further comprises a lens 16 disposed to receive UVC light from the UVC LED 14. The UVC LED 14 is electrically power and includes electrical leads 18 to receive such electrical power. The UVC LED 14 emits light having a wavelength in the UVC wavelength range and in certain implementations herein emits light in the range of from 250 nm to 280 nm, 250 nm to 275 nm, 260 nm to 270 nm, for example, possibly having a peak wavelength in one or more of these range, e.g., possibly at 265 nm. Likewise, the lens 16 may comprise material optically transmissive to UVC light such as light in the wavelength range of the UVC light emitted by the UVC LED 14. In some implementations, for example, the lens 16 comprises a fused silica lens comprising fused silica, which is transmissive to UVC light. In some implementations, for example, the lens 16 is optically transmissive to light in the wavelength range of from 220 nm to 290 nm, 220 nm to 280 nm, 250 nm to 280 nm, 250 nm to 275 nm, 260 nm to 275 nm, 260 nm to 270 nm, e.g., 265 nm, or any range formed by any of these values.

As discussed above, in some implementations, the lens comprises fused silica. In various implementations, the lens may comprise fused silica glass having a transmittance (e.g. internal transmittance or transmittance corrected to reduce or possibly eliminate the effects of scattering and of reflection from surfaces) of UVC light with 245-280 nm wavelength of least 95% for a 10 mm thickness of the fused silica glass although in other implementations this transmittance is at least 50%, 55%, 60%, 65%, 70%, 75%. 80%, 85%, 90%, 94%, 96%, 98%, 99%, 99.9%, or 100% or any range formed by any of these values or possibly more or less. In various implementations, the OH (e.g., Hydroxyl) content is not larger than 5 ppm although in other implementations the OH content is not larger than 0.05 ppm, 0.01 ppm, 0.5 ppm, 1 ppm, 2 ppm, 3 ppm, 4 ppm, 6 ppm, 8 ppm, 10 ppm, 20 ppm, 30 ppm, 40 ppm, 50 ppm, 60 ppm, 70 ppm, 80 ppm, 90 ppm, 100 ppm, 125 ppm, 150 ppm, 200 ppm, 300 ppm, 400 ppm, or 500 ppm or any range formed by any of these values or possibly more or less. Additionally, in various implementations, a content of Li, Na, K, Mg, Ca and Cu each are smaller than 0.1 ppm although in some implementations the content of any one or more possibly each of Li, Na, K, Mg, Ca and Cu are smaller than 0.001 ppm, 0.005 ppm, 0.01 ppm, 0.05 ppm, 0.2 ppm, 0.3 ppm, 0.4 ppm, 0.5 ppm, 0.6 ppm, 0.7 ppm, 0.8 ppm, 0.9 ppm, 1 ppm, 1.25 ppm, 1.50 ppm, 2.00 ppm, 3.00 ppm, 4.00 ppm, or 5.00 ppm or any range formed by any of these values or possibly more or less.

In some implementations, the glass has a viscosity coefficient at 1215° C. of at least $10^{11.5}$ Pa·s: and a Cu ion diffusion coefficient of not larger than $1\times10^{-10}$ m$^2$/sec in a depth range of greater than 20 μm up to 100 μm, from the surface, when leaving to stand at 1050° C. in air for 24 hours. However, the glass need not be so limited as other implementations are possible.

In some case, the glass may be fabricated by crystobalitizing powdery silica raw material and then, fusing the crystobalitized silica material in a non-reducing atmosphere. However, the method of manufacture should not be so limited.

In some implementations, the fused silica glass may exhibit a high transmittance of ultraviolet, visible and infrared rays, may have high purity and heat resistance, and may exhibits a reduced diffusion rate of metal impurities or any combination of these traits.

As illustrated the lens 16 may comprise a plano-convex lens although other lenses may be employed. In various implementations, the lens 16 is configured to collimate the UVC light from the UVC LED 14. In various implementations, the lens 16 comprises a positive power lens. In various designs, the lens 16 is positioned a focal length away from the UVC LED 14 although the lens and the UVC LED may be separated by other distances including at a distance sufficiently close to collimate most of the light. In various designs, the lens 16 reduces the divergence of UVC light output by the UVC LED 14 which can have a divergence angle, for example of at least 120°, 130°, 140°, 150°, 160°, 170°, or 1800 or in any range formed by any of these values. The lens 16 may also comprise an aspheric lens having, for example, at least one aspheric surface that refracts light incident thereon and/or transmitted therethrough.

In various implementations, the lens 16 may, for example, reduce the divergence to 60°, 500 40°, 30°, 20°, 10°, 15°, 5°, 3°, or 1° or any value between any of these ranges or possibly larger or smaller. For example, the divergence may be between 400 and 5°, 400 and 10°, 400 and 15°, 300 and 5°, 300 and 10°, 300 and 15°, 200 and 5°, 200 and 10°, 200 and 15°, e.g., 18°. In some designs, most, if not all, the light or possibly at least 20%, 30%, 40%, 50%, 60%, 70%, 80%, 90%, 95%, 98%, 99%, or 100% of the light (or any range formed by any of these values) output by these UVC light sources 12 are directed forward and project light forward (e.g., mostly in the Z direction as shown by the XYZ coordinate system) or within an angular range of ±60°, ±50°, ±40°, ±30°, ±20°, ±10°, ±15°, ±5°, ±3°, or ±1° of the forward (Z) direction or any range formed by any of these values, or possibly larger or smaller. In some designs, the divergence angle and/or beam width varies with effective focal length. In various designs, the effective focal length may be, for example, 15 mm, 14 mm, 13 mm, 12 mm, 11 mm, 10 mm, 9 mm, 8 mm, 7 mm, 6 mm, 5 mm, 4 mm, 3 mm, 2 mm, or 1 mm or any range formed by any of these values. Focal lengths outside these ranges are also possible. Similarly, the distance from the UVC LED 14 and the lens 16 may be 15 mm, 14 mm, 13 mm, 12 mm, 11 mm, 10 mm, 9 mm, 8 mm, 7 mm, 6 mm, 5 mm, 4 mm, 3 mm, 2 mm, or 1 mm or any range formed by any of these values although other distances, for example, outside such ranges may be possible. In some designs the distance between UVC LED 14 and the lens 16 may be the same although in other designs the distance is not identical.

In the design illustrated in FIG. 2, the UVC light source 10 includes a optics mount or outer optics retaining housing or retainer 20 to which the UVC LED 14 and/or lens 16 are attached. The optics mount or outer optics retaining housing 20 has a channel or cavity 22 therein for propagation of UVC light (represented by ray 24) from the UVC LED 14 to the lens 16. The channel 22 may comprise sidewalls 26 that are reflective to the UVC light emitted by the UVC LED 14 such that UVC light from the LED can propagate from the LED to the lens 16 by reflecting off these sidewalls. The sidewalls may be sloped or have other shapes. The channel 22 has a forward end and a rearward end with the lens 16 closer to the forward end and the LED 14 closer to the rearward end. In various designs, the optics mount or outer optics retaining housing 20 has a size, e.g., length, such that the lens 16 is positioned a focal length away from the UVC LED 14 although the lens and the LED may be separated by other distances including distance sufficiently close to collimate most of the light. In some implementations the distance is such to at least reduce the divergence angle of the UVC light exiting the UVC LED 14. As discussed above, the reflective sidewalls 26 of the channel or cavity through which light propagates from the UVC LED 14 to the lens 16 may be sloped. Such sloping may provide for collection of UVC light from the UVC LED 14 at a wider angle and directing to the lens 16 such that the light can be transmitted by the lens into a smaller or narrower angle. Likewise, the angle of the sidewall (e.g., the slope thereof), together with possibly the focal length of the lens 16 and/or the distance between the lens and the UVC LED 14, may influence the divergence angle of light exiting the lens 16 and emitted from the UVC light source 12. The optics mount or outer optics retaining housing 20 may comprise metal such as aluminum in some designs.

As illustrated in FIG. 1, the UVC light projection unit 10 further comprises an elongate support or arm (also referred to herein as an elongate support member) 28 on which the UVC light source 12 is supported. This elongate support or arm or elongate member 28 may in certain implementations be thinner than long. In various implementations, elongate support or arm or elongate member 28 has a profile that reduces blockage of or resistance to air flowing through the HVAC device, e.g., duct, along the length of the HVAC device, e.g., duct. Accordingly, in some implementations, the elongate support or arm or elongate member 28 has a thickness that faces the air flow that is smaller than its depth and width. In some implementation, the optics mount or outer optics retaining housing 20 and the arm 28 comprise a monolithic structure while in other implementations, optics housing region 20 and the arm 28 are separate components fastened or secured together. In some implementations, the elongate member or support arm 28 comprises metal such as aluminum in some designs. Other materials, however, may possibly be employed.

The UVC LED 14 may generate heat when being activated. Likewise, the UVC light source 10 includes a heat sink 29 and heat sink radiative fins 30. In the design shown in FIG. 1, these fins extend radially from the UVC light source 12. In various implementations, the heat sink radiate fins 30 are coupled to the heat sink 29 in which the UVC LED 14 is situated so as to dissipate heat generated by the UVC LED. In the design shown, for example, the UVC LED 14 is mounted on a platform such as a printed circuit board (PCB) 27, which may be disposed on the heat sink 29, which may serve to transfer heat from the UVC LED to the heat dissipation fins 30. In some implementations, the heat sink 29 and fins 30 comprise a monolithic structure such as a monolithic metal structure although other designs are possible. As illustrated, the small PCB board 27 is on the front center of the heatsink 29. In some implementations, the heat sink 29 and/or heat sink radiative fins 30 comprise metal such as aluminum.

The example shown in FIG. 1 also includes a base 32 at one end of the elongate support or arm 28. In the example shown, the UVC light source 10 is at another end of the elongate support or arm 28 opposite the base 32. The base 32 is configured to be attached to another structure such as the mounting platform (see FIG. 3) that is configured to attach to the HVAC device (e.g., the duct, plenum device, or plenum). Various examples below are discussed in the context of the HVAC device being an air duct, however, the HVAC device could alternatively be a plenum device, a plenum or other HVAC device through which air flows.

Figure 3:
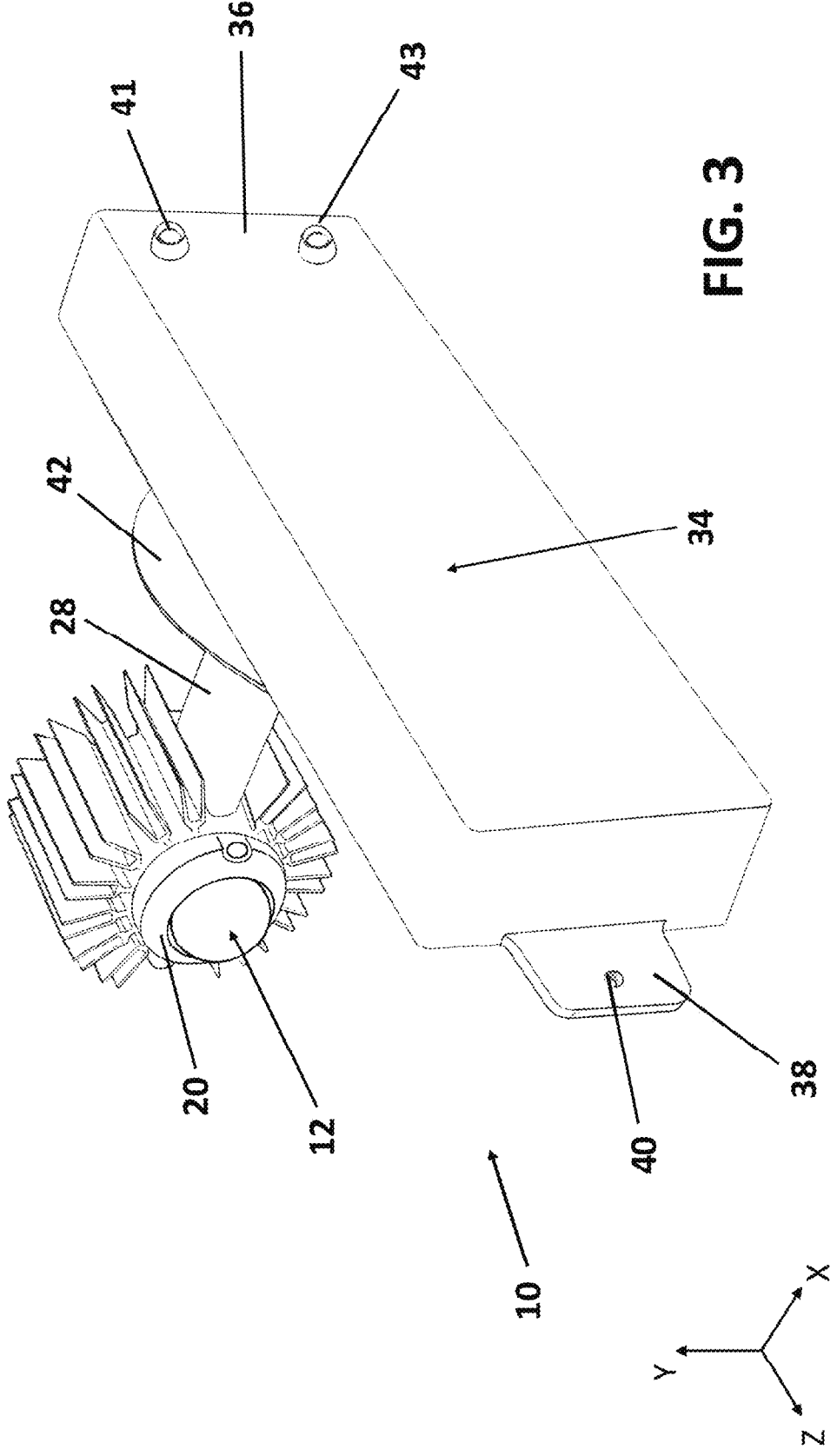
FIG. 3 is a perspective view of an HVAC UVC light projection unit for providing UVC illumination within an HVAC device such as an air duct or plenum device (e.g., plenum) comprising a mounting platform configured to mount on the outside of the HVAC device. An elongate support extends transversely from the mounting platform such that when the mounting platform is mounted on the outside of the HVAC device, the elongate support is within the HVAC device. The elongate support and/or a portion of the mounting platform can extend into and/or through a hole in the HVAC device. The HVAC UVC light projection unit has a single UVC light source. This UVC light source is supported on the elongate support inside the HVAC device and is configured to be oriented so as to direct UVC light generally along the longitudinal direction of said HVAC device.

FIG. 3 shows the HVAC UVC light projection unit 10 having a mounting platform 34. In the illustrated design, the elongate support or arm 28 is connected to the mounting platform 34. In various implementations, the mounting platform 34 is configured to attached to the wall of the duct on the outside of the duct while the elongate support or arm 28 and/or a portion of the mounting platform and/or other component extends into the duct through a hole in the duct. Also, in various implementations, the elongate support or arm 28 has a low profile to reduced air resistance. The elongate support or arm 28 may for example have a smaller thickness (e.g., in the y direction) than width (in the x direction) and depth (e.g., in the z-direction).

In the example HVAC UVC light projection unit 10 shown in FIG. 3, the mounting platform 34 includes a housing 36 configured to house electronics, for example, for driving the UVC LED 14. Also as illustrated, the mounting platform 34 includes portions 38 for securing the mounting platform to the duct. In the example shown, these portions 38 include through holes for screwing the mounting platform 34 to the duct. FIG. 3 illustrates the screws 40 in the through holes. Such screws 40 may comprise, for example, self-tapping screw such as, e.g., sheet metal screws.

In the example shown, the portions 38 of the mounting platform 34 with through holes comprise portions of the housing 36 that extend outward. In some implementations, these portions 38 may comprise, for example tabs or extensions, that extend outward and may or may not be part of the housing 38. In some implementations, these tabs or extension 34 may have a thickness that is reduced compared to the thickness of other portions of the housing 38, e.g., containing electronics such as for driving the UVC LED 14. Such reduced thickness may permit shorter screws 40 to be used. In the example shown, the portions 38 of the mounting platform 34 for securing the mounting platform to the duct are on opposite sides (e.g., left and right sides) of the mounting platform and housing. Other configurations are possible.

As illustrated in FIG. 3, the mounting platform 34 further may include one or more cover pieces 42 for covering a portion of a hole cut into the duct. In various implementations, for example, the hole is 2.0, 2.5, 3.0, 3.5, 4.0, 4.5, 5.0 or 6.0 inches across, e.g., in diameter or in any range formed by any of these values. Such a size may allow the heatsink fins 30 to fit through the hole during insertion of the UVC light source 12.

These cover pieces 42 may comprise extensions of the housing 36 in some cases. These cover pieces 42 may also comprise separate components, for example, attached to the housing 36.

The mounting platform 34 shown in FIG. 3 also includes warning lights or LEDs 41, 43. One light 41 indicates the power to the unit is ON. The second warning light 43 shows that the UVC LEDs 14 are in operation.

The example shown in FIG. 3 includes a single UVC light source 12. The elongate support member 28 extends in the transverse direction with respect to the mounting platform 34 and the duct. In particular, in the example shown, the elongate support member 28 extends in a direction normal to the mounting platform 34 and/or the bottom of the mounting platform. Accordingly, when the mounting platform 34 is attached to the outside of the wall of the duct, the elongate support member 28 can position the UVC light source 12 inside the duct. In some implementations, the elongate member or arm 28, the housing 36 or other portion of the mounting platform 34, or other components or any combination of these may extend into and/or pass through the hole in the wall of the duct such that the UVC light source 12 may be inside the duct.

As shown, both the UVC light source 12 and the UVC light emitted therefrom is configured to be directed along the longitudinal direction (e.g., in the Z direction per the XYZ coordinate system shown in lower left of FIG. 3) along the length of the air duct. For example, in some designs, the lens 16 has an optical axis that is configured to be directed along the longitudinal direction (e.g., in the Z direction) along the length of the air duct. As the air is flowing along the length of the duct or shaft, directing the UVC light along the length of the duct or shaft (either opposite to the flow of air or with the flow of air) provides for a longer time over which a portion of the air is exposed to the UVC light, which can increase the effectiveness of the sterilization and/or inactivation process.

With only one UVC light source 12, this UVC HVAC light projection unit 10 may output radiant flux of, for example, 30, 40, 50, 60, 70, 80, 90, 100, 110, 120, 130, 140, 150, 160, 170, 180, 190, or 200 mW or any range formed by any of these values, e.g., 100 to 200 mW. The radiant flux output by some designs may be larger or smaller. Various implementations of the UVC HVAC light projection unit 10 having the same or a different number of UVC light sources 12 may output radiant flux of, for example, 10, 20, 30, 40, 50, 60, 70, 80, 90, 100, 110, 120, 130, 140, 150, 160, 170, 180, 190, 200, 220, 250, 275, 300, 350, 400, 450, 500, 600, 700, 800, 900, 1000, 1500, 2000, 2500, 3000, 3500, or 4000 mW or any range formed by any of these values or other amounts as well.

Figure 4:
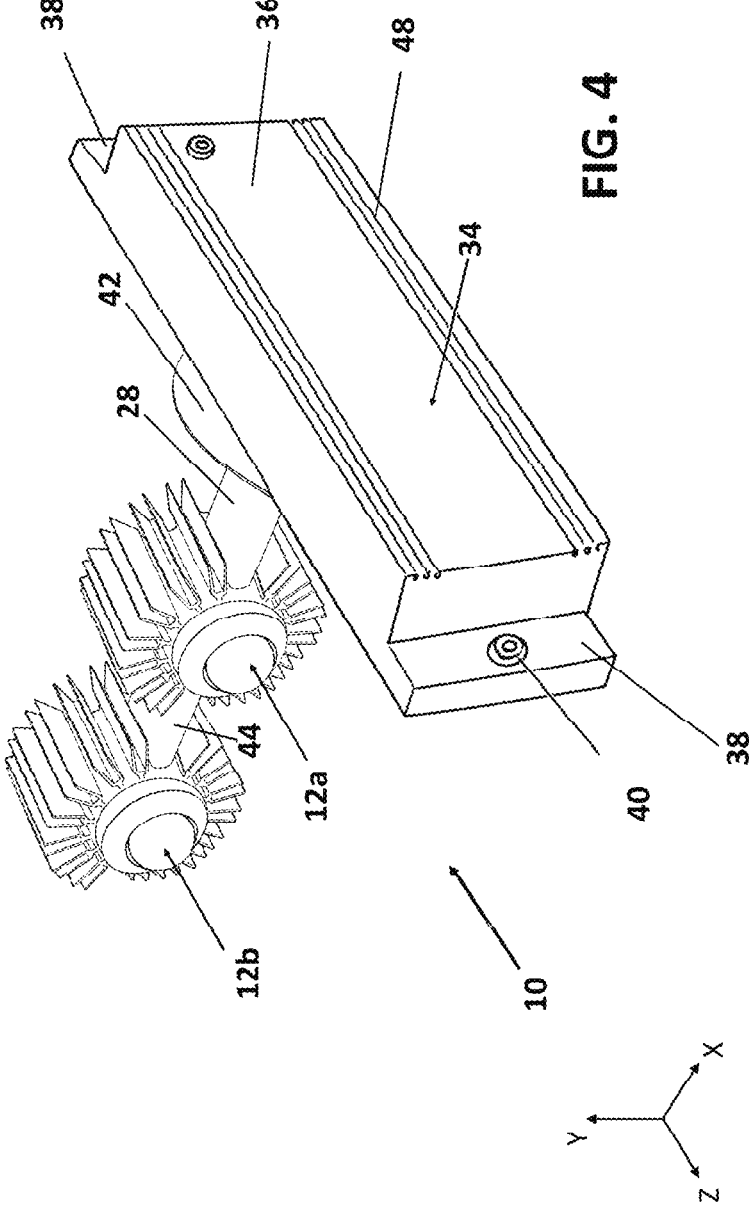
FIG. 4 is a perspective view of an HVAC UVC light projection unit for providing UVC illumination within an HVAC device such as an air duct or plenum device (e.g., plenum) similar to that shown in FIG. 3 with two, and only two, UVC light sources.

Other UVC HVAC light projection units 10 may have more UVC light sources 12. FIGS. 4 and 5, for example, show HVAC UVC light projection units 10 having two and three UVC light sources, respectively.

As shown, the HVAC UVC light projection unit 10 in FIG. 4 comprises two (and only two) UVC light sources 12, a first UVC light source 12a spaced apart from a second UVC light source 12b in the transverse direction. The first UVC light source 12a is supported by the elongate support member or arm 28 and the second UVC light source 12b is supported by another elongate support member 44 connected to the first UVC light source. In the example shown, both elongate support members (first and second) 28, 44 extend in the transverse direction, in this example in the same direction, with respect to the mounting platform 34 and the duct, for example, orthogonal to the mounting platform and/or the bottom of the mounting platform. Accordingly, when the mounting platform 34 is attached to the outside of the wall of the duct, at least a portion of the elongate support member 28 can be within the duct and can position the UVC light source 12 inside the duct. In some implementations, the elongate support 28, the housing 36 or other portion of the mounting platform 34, or other component or any combination thereof may extend into and/or pass through the hole in the wall of the duct. Also, in various implementations, elongate support or arm 28 has a low profile to reduced air resistance. The elongate support or arm 28 may for example have a smaller thickness (e.g., in the y direction) than width (in the x direction) and depth (e.g., in the z-direction).

Other configurations are possible. For example, the second elongate support member 44 need not extend in an identical direction as the first elongate support member 28. In other designs, the first and second light sources 12a, 12b may supported on the same elongate support or arm 28. Nevertheless, in some such cases when the mounting platform 34 is attached to the outside of the wall of the duct, the elongate support member 28 can position the UVC light source 12 inside the duct. As discussed above, in some implementations, the elongate support 28, the housing 36 or other portion of the mounting platform 34, or other component or any combination thereof may extend into and/or pass through the hole in the wall of the duct.

As shown, both the first and second light sources 12a, 12b are directed in the same direction and are configured to be directed along the longitudinal direction (e.g., Z direction) along the length of the air duct. As the air is flowing along the length of the duct or shaft, directing the UVC light along the length of the duct or shaft (either opposite to the flow of air or with the flow of air) provide for a longer time over which a portion of the air is exposed to the UVC light, which can increase the effectiveness of the sterilization and/or inactivation process.

The two UVC light sources in the HVAC UVC light 10 shown in FIG. 4 may together output a radiant flux, for example, of 50, 70, 80, 90, 100, 110, 120, 130, 140, 150, 160, 170, 180, 190, 200, 210, 220, 230, 240, or 250 mW or any range formed by any of these values, e.g., 100 to 200 mW. The radiant flux output by some designs may be larger or smaller. Various implementations of the UVC HVAC light projection unit 10 having the same or a different number of UVC light sources 12 may output radiant flux of, for example, 30, 40, 50, 60, 70, 80, 90, 100, 110, 120, 130, 140, 150, 160, 170, 180, 190, 200, 220, 250, 275, 300, 350, 400, 450, 500, 600, 700, 800, 900, 1000, 1500, 2000, 2500, 3000, 3500, or 4000 mW or any range formed by any of these values or other amounts as well.

The HVAC UVC light projection unit 10 shown in FIG. 5 comprises three (and only three) UVC light sources 12, a first UVC light source 12a spaced apart from a second UVC light source 12b in the transverse direction and a third UVC light source 12c spaced apart from the first and second UVC light sources in the transverse direction. The first UVC light source 12a is supported by the elongate support member or arm 28 and the second UVC light source 12b is supported by another elongate support member 44 connected to the first UVC light source. The third UVC light source 12c is supported by another elongate support member 46 connected to the second UVC light source 12b. In the example shown, the three elongate support members (first, second, and third) 28, 44, 46 extend in the transverse direction, in this example in the same direction, with respect to the mounting platform 34 and the duct. In particular, in the example of FIG. 5, the three elongate support members (first, second, and third) 28, 44, 46 extend in a direction normal to the mounting platform 34, e.g., the bottom of the mounting platform. Accordingly, in some such cases when the mounting platform 34 is attached to the outside of the wall of the duct, the UVC light sources 12a, 12b, 12c can be inside the duct. As discussed above, in some implementations, the elongate support 28, the housing 36 or other portion of the mounting platform 34, or other component or any combination thereof may extend into and/or pass through the hole in the wall of the duct. Also, in various implementations, the elongate support or arm 28 has a low profile to reduced air resistance. The elongate support or arm 28 may for example have a smaller thickness (e.g., in the y direction) than width (in the x direction) and depth (e.g., in the z-direction).

Other configurations, however, are possible. For example, the second and/or third elongate support member 44, 46 need not extend in an identical direction as the first elongate support member 28 and/or as each other. In other designs, the first, second, and third light sources 12a, 12b, or different combinations of these (first and second or second and third) may supported on the same elongate support or arm 28, 44, 46. Nevertheless, in at least some such cases, when the mounting platform 34 is attached to the outside of the wall of the duct, the UVC light sources 12a, 12b, 12c can be inside the duct. As discussed above, in some implementations, the elongate support 28, the housing 36 or other portion of the mounting platform 34, or other component or any combination thereof may extend into and/or pass through the hole in the wall of the duct.

As shown, the first, second, and third light sources 12a, 12b, 12c are directed in the same direction and are configured to be directed along the longitudinal direction (e.g., in the direction of the Z axis) along the length of the air duct. As the air is flowing along the length of the duct or shaft, directing the UVC light along the length of the duct or shaft (either opposite to the flow of air or with the flow of air) provide for a longer time over which a portion of the air is exposed to the UVC light, which can increase the effectiveness of the sterilization and/or inactivation process.

The three UVC light sources 12 in the HVAC UVC light 10 shown in FIG. 4 may together output radiant flux, for example, of 150, 160, 170, 180, 190, 200, 210, 220, 230, 240, 250, 260, 270, 280, 290, 300, 310, 320, 330, 340, or 350 mW or any range formed by any of these values, e.g., 180 to 250 mW. The radiant flux output by some designs may be larger or smaller. Various implementations of the UVC HVAC light projection unit 10 having the same or a different number of UVC light sources 12 may output radiant flux of, for example, 30, 40, 50, 60, 70, 80, 90, 100, 110, 120, 130, 140, 150, 160, 170, 180, 190, 200, 220, 250, 275, 300, 350, 400, 450, 500, 600, 700, 800, 900, 1000, 1500, 2000, 2500, 3000, 3500, or 4000 mW or any range formed by any of these values or other amounts as well.

The mounting platforms 34 shown in FIGS. 4 and 5 include portions 38 for securing the mounting platform to the duct. In the example shown, these portions 38 include through holes for screwing the mounting platform 34 to the duct. FIG. 3 illustrates the screws 40 in the through holes. Such screws 40 may comprise, for example, self-tapping screw such as, e.g., sheet metal screws.

In the example shown, the portions of the mounting platform 34 with through holes comprise portions of the mounting platform that extend outward. In the examples shown, these portions 38, which extend outward, are parts of the housing 36. In some implementations, these extensions 38 have a thickness that is reduced compared to the thickness of other portions of the housing 36, e.g., containing electronics such as for driving the UVC LED 14. Such reduced thickness may permit shorter screws 40 to be used. In the example shown, the portions 38 of the mounting platform 34 for securing the mounting platform to the duct are on opposite sides (e.g., left and right sides) of the mounting platform and housing. Other configurations are possible.

The mounting platforms 34 shown in FIGS. 4 and 5 also have heat dissipation grooves 48. In the examples shown, these heat dissipation grooves 48 are in the housing 36.

Figure 6:
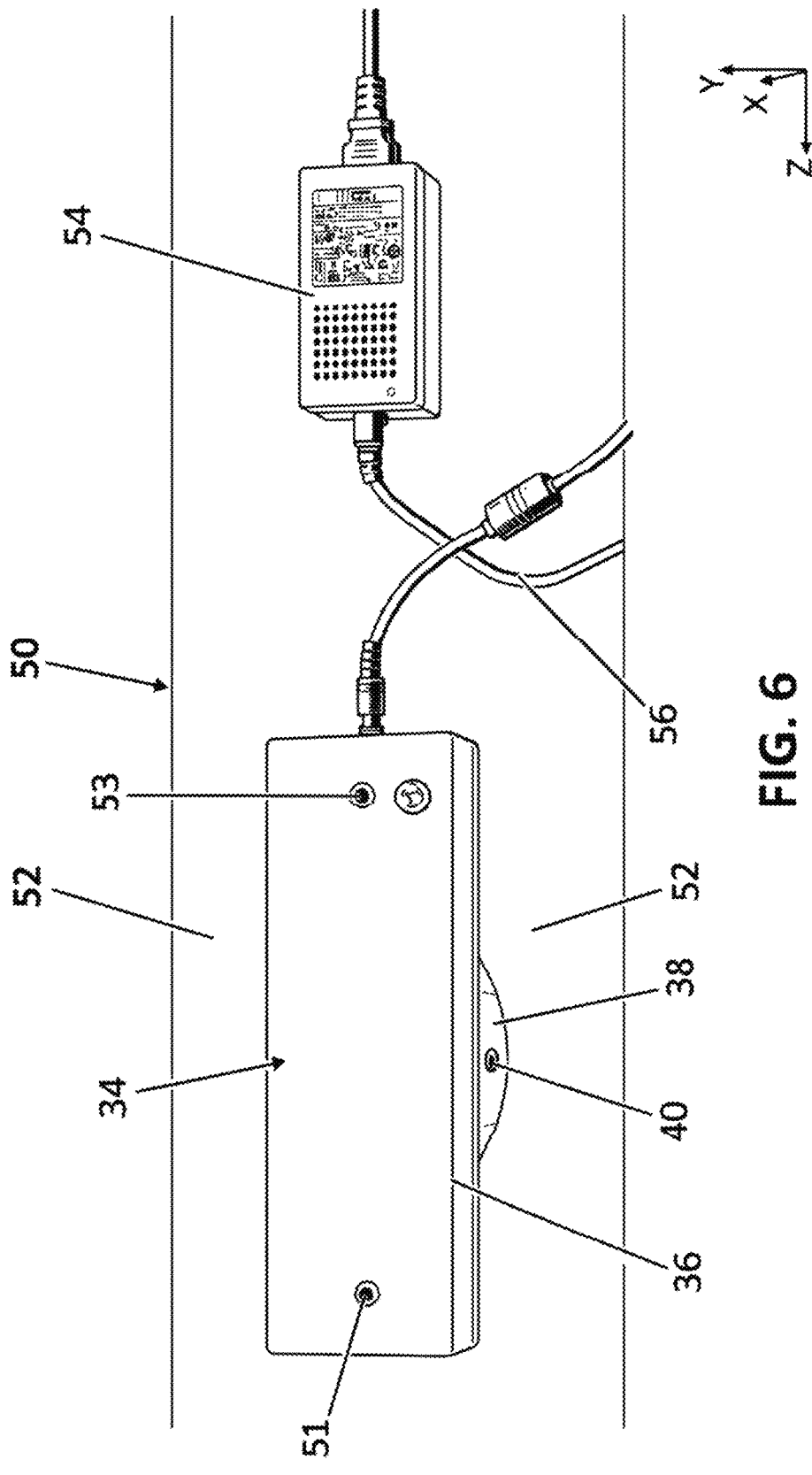
FIG. 6 is a perspective view of the mounting platform secured to (e.g., screwed to) the outside of an air duct.

FIG. 6 shows the mounting platform 34 mounted on the air duct 50. The air duct 50 comprises walls (e.g., sidewalls) 52 comprising, for example, sheet metal. The mounting platform 34 is secured to the air duct 50 and, in particular, to the walls/sidewalls 52 of the duct via screws 40 through holes in portions of the housing 36. As discussed above, the screws 40 may comprise self-taping screws. Additionally, these screws 40 may comprise sheet metal screws. Through holes in 51, 53 in the housing 36 can receive the screws to secure the mounting platform 34 to the duct 50. As further illustrated in FIGS. 7 and 8 below, the mounting platform 34 is oriented such that the UVC light source 12 is pointed along the longitudinal direction (Z direction) of the duct 50 so that UVC light (e.g., most of the UVC light) emitted by the UCV light source is directed along the longitudinal direction and propagates along the length of the duct.

FIG. 6 additionally shows a power supply 54 electrically connected to the electronics in the mounting platform 34 via an electrical line 56 such as an electrical cable or wiring.

Although the power supply 54 is shown separately, in some designs, the power supply may be integrated inside the mounting platform 34.

Figure 7:
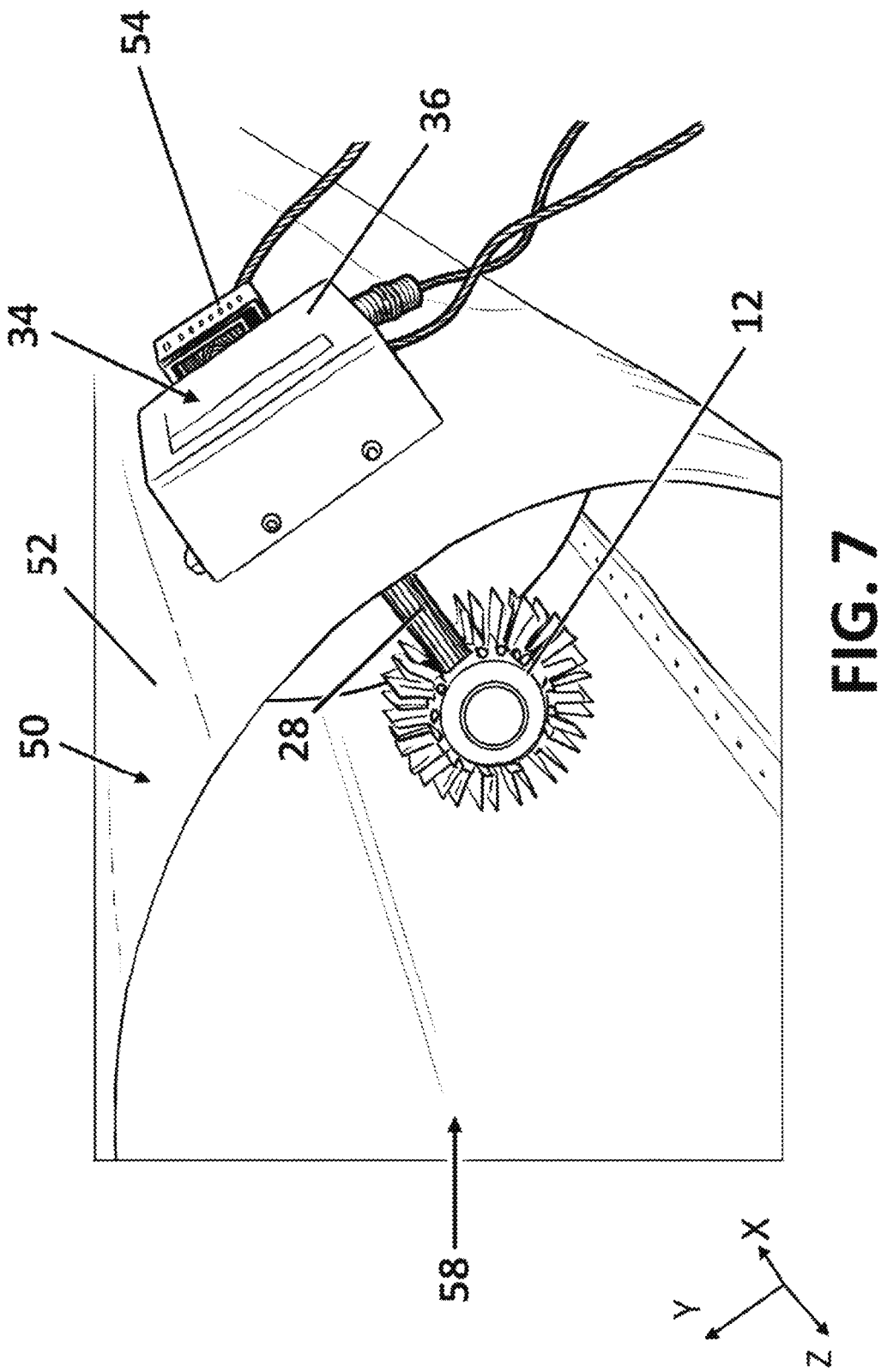
FIG. 7 is another perspective view of the mounting platform secured to (e.g., screwed to) the outside of the air duct additionally providing a view inside the duct.

Another view of the UVC light projection unit 10 mounted on the duct 50 is shown in FIG. 7. This view also shows the inside 58 of the duct 50 containing the UVC light source 12 therein. The mounting platform 34 is shown secured to the wall 52 of the duct 50. The elongate support 28 is shown extending into the inside 58 of the duct 50 such that the UVC light source 12 is positioned inside the duct. As illustrated, the UVC light projection unit 10 (e.g., mounting platform 34) is oriented such that the UVC light source 12 is pointed along the longitudinal direction (e.g., in Z direction) of the duct 50 so that UVC light (e.g., most of the UVC light) emitted by the UCV light source is directed along the longitudinal direction and propagates along the length of the duct.

Figure 8:
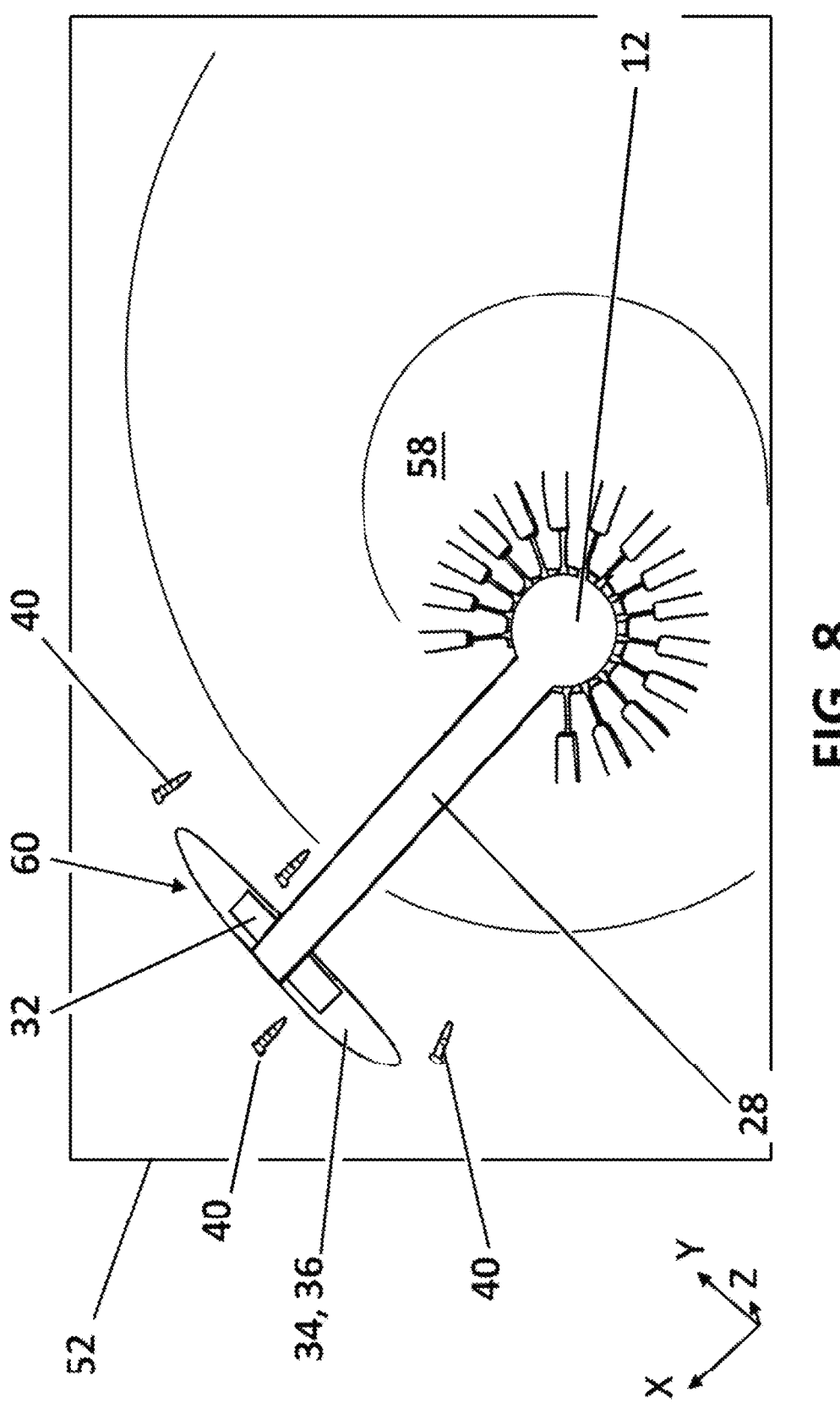
FIG. 8 is a perspective view of the elongate support extending from the mounting platform via a hole in the duct. As illustrated, the UVC light source is oriented so as to point along the length of the duct such that UVC light (e.g., most the UVC light) is directed along the along the length of the duct.

Another view of the inside 58 of the duct 50 is shown in FIG. 8. FIG. 8 shows the hole 60 in the wall 52 of the duct 50 that enables the UVC light source 12 to be connected to the mounting platform 34. As discussed above, the mounting platform 34, in addition to securing the UVC light projection unit 10 to the duct 50, may house electronics therein for driving the UVC light source(s) 12 and the UVC LED(s) 14. In such cases, the mounting platform 34 may comprise a control box for controlling operation of the light source(s) 12. As illustrated, the UVC light source 12 is on the elongate support 28. In various implementations, electrical lines such as electrical wires and/or cables electrically connect the electronics within the mounting platform 34 to the UVC light source 12 such as the UVC LED 14. Such electrical lines or wires maybe including in and/or on and/or supported by the elongate support(s) 28, 44, 46. In the example shown in FIG. 8, the elongate support 28 is connected to the bottom of the mounting platform 34 (e.g., bottom of the housing 36) via the base 32. The bottom of the mounting platform 34 (e.g., bottom of the housing 36) to which the base 32 is attached can be seen through the hole 60 in the wall 52 of the duct 50. Other configurations are possible. For example, the housing 36 or other portions of the mounting platform 34 may extend through the hole 60 in the duct 50, e.g., in the hole in the wall 52 of the duct. In various implementations, this hole 60 in the wall of the duct may be 2.5, 3.0, 3.5, 4.0, 4.5, 5.0 or 6.0 inches across (e.g., in diameter) or any range formed by any of these values. In various implementation the size of the hole 60 is sufficiently large such that the light source(s) 12 including the heat dissipation fins 30 can be inserted into the duct through the hole.

As illustrated, the length of elongate support or arm 28 extend in a direction orthogonal or normal to the mounting platform 34, for example, orthogonal or normal to the bottom of the mounting platform 34.

The screws 40 that secure the mounting platform 34 to the duct 50, e.g., to the wall 52 of the duct, can be seen penetrating into the inside 58 of the duct. As discussed above, these screws 40 may be self-tapping screw and/or sheet metal screws.

FIG. 8 also shows the UVC light source 10 disposed within the inside 58 of the duct 50. Moreover, the UVC light source 10 is oriented so as to be directed along the longitudinal direction e.g., Z direction, along the length of the duct 50. Likewise, the UVC light source 10 is oriented to direct UVC light (e.g., most of the UVC light) output by the UVC light source along the length of the duct 50.

Without subscribing to any scientific theory, UVC light may potentially render certain viruses and/or bacteria inactive as a result of the absorption of UVC wavelengths by DNA. Accordingly, the UVC light sources 10 and UVC LEDs 14 employed in the UVC light projection unit 12 are configured to emit UVC light capable of destroying, disabling or weakening virus and bacteria and/or the reproduction thereof. This light output by the LEDs 14 may, for example, comprise light within the range of from 250 nm to 290 nm, 250 nm to 280 nm, 260 nm to 290 nm, 260 nm to 280 nm, 260 nm to 270 nm, 262 nm to 268 nm, for example, 265 nm in wavelength. In various implementations, most, all or nearly all of the light emitted from the UVC LEDs 14 and the corresponding UVC light source 12 may comprise UVC light in the wavelength range of 250 nm to 290 nm or 250 nm to 280 nm or 258 to 274 nm or 260 to 271 nm or 261, 262, 263, 264 or 265 to 266, 267, 268, 269, 270, 271, 272, 273, 274, 276 nm, or 260 to 280 or 260 to 270 nm or 263 nm to 267 nm, 265 nm to 275 nm or at 265 nm or any range formed by any of these percentages and/or wavelength values, although values outside these ranges are also possible. Similarly, in various implementations, the UVC light output by the UVC light projection unit 10, the UVC light source 12, the UVC LED 14 or any combination of these may have a peak in the wavelength range of 250 nm to 280 nm or 258 to 274 nm or 260 to 271 nm or 261, 262, 263, 264 or 265 to 266, 267, 268, 269, 270, 271, 272, 273, 274, 276 nm, or 260 to 280 or 260 to 270 nm or 263 nm to 267 nm, 265 nm to 275 nm or at 265 nm or any range formed by any of these percentages and/or wavelength values, although values outside these ranges are also possible.

Figure 9:
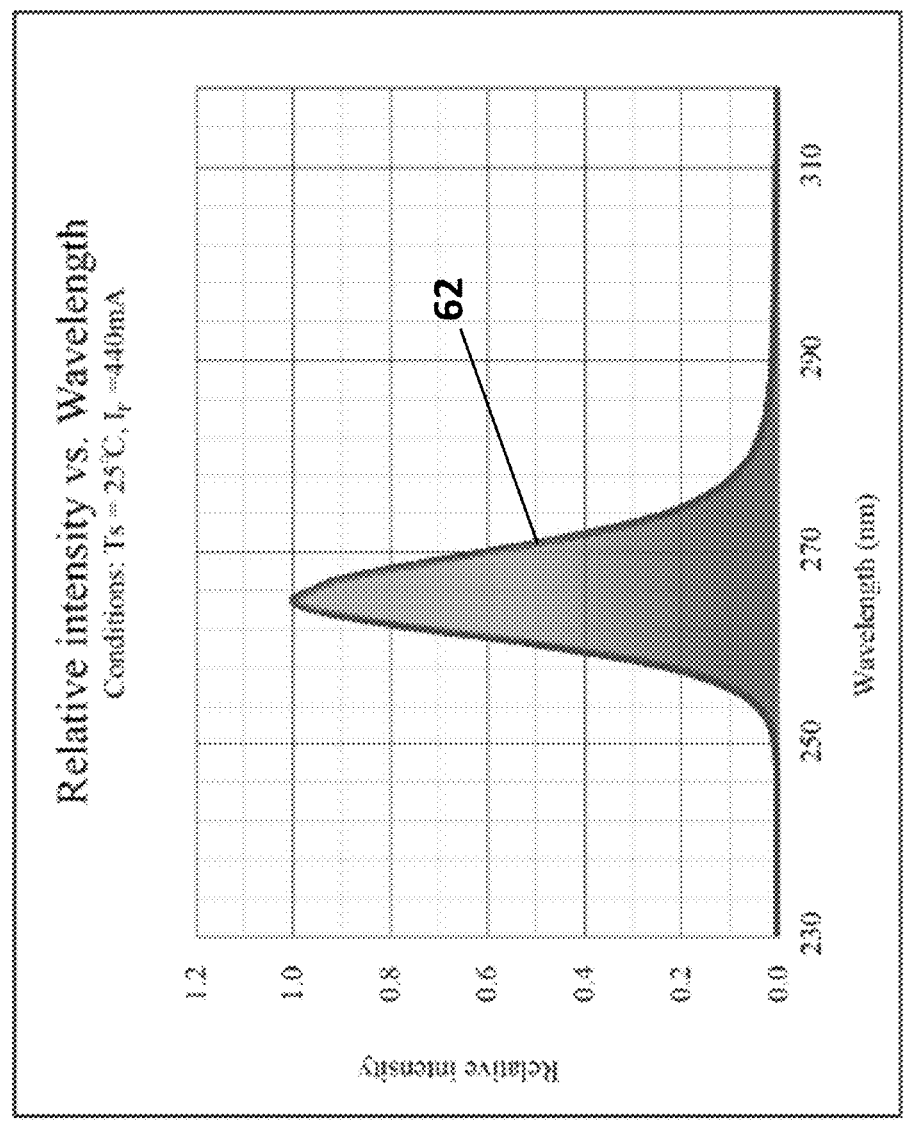
FIG. 9 is a plot on axis of intensity (in relative units) and wavelength (in nanometers) showing the wavelength distribution of light output by the UVC LED.

Accordingly, various designs comprise the UVC light source 12 or UVC light sources (12a, 12b, 12c) such as shown in FIGS. 3-5 have a spectral distribution such as shown in FIG. 9. FIG. 9 is a plot on axis of intensity (in relative units) and wavelength (in nanometers) showing the wavelength distribution of light output by the UVC light sources 12 and/or UVC LED 14. This intensity versus wavelength curve 62 has a wavelength peak at 265 nm. This distribution 62 also has a full width have maximum from about 260.5 nm to 271 nm. Accordingly, in various implementations, the UVC light source(s) 12 and/or UVC LED(s) 14 may, for example, be configured to emit more than 50%, 60%, 70%, 80%, 90%, 95%, 97%, 98% 99%, 99.9% or 100% of the light output therefrom in the UVC range, in the wavelength range from 250 nm to 280 nm or 258 to 274 nm or 260 to 271 nm or 261, 262, 263, 264 or 265 to 266, 267, 268, 269, 270, 271, 272, 273, 274, 276 nm, or 260 to 280 or 260 to 270 nm or 263 nm to 267 nm, 265 nm to 275 nm or at 265 nm or any range formed by any of these percentages and/or wavelength values, although values outside these ranges are also possible.

Figure 10:
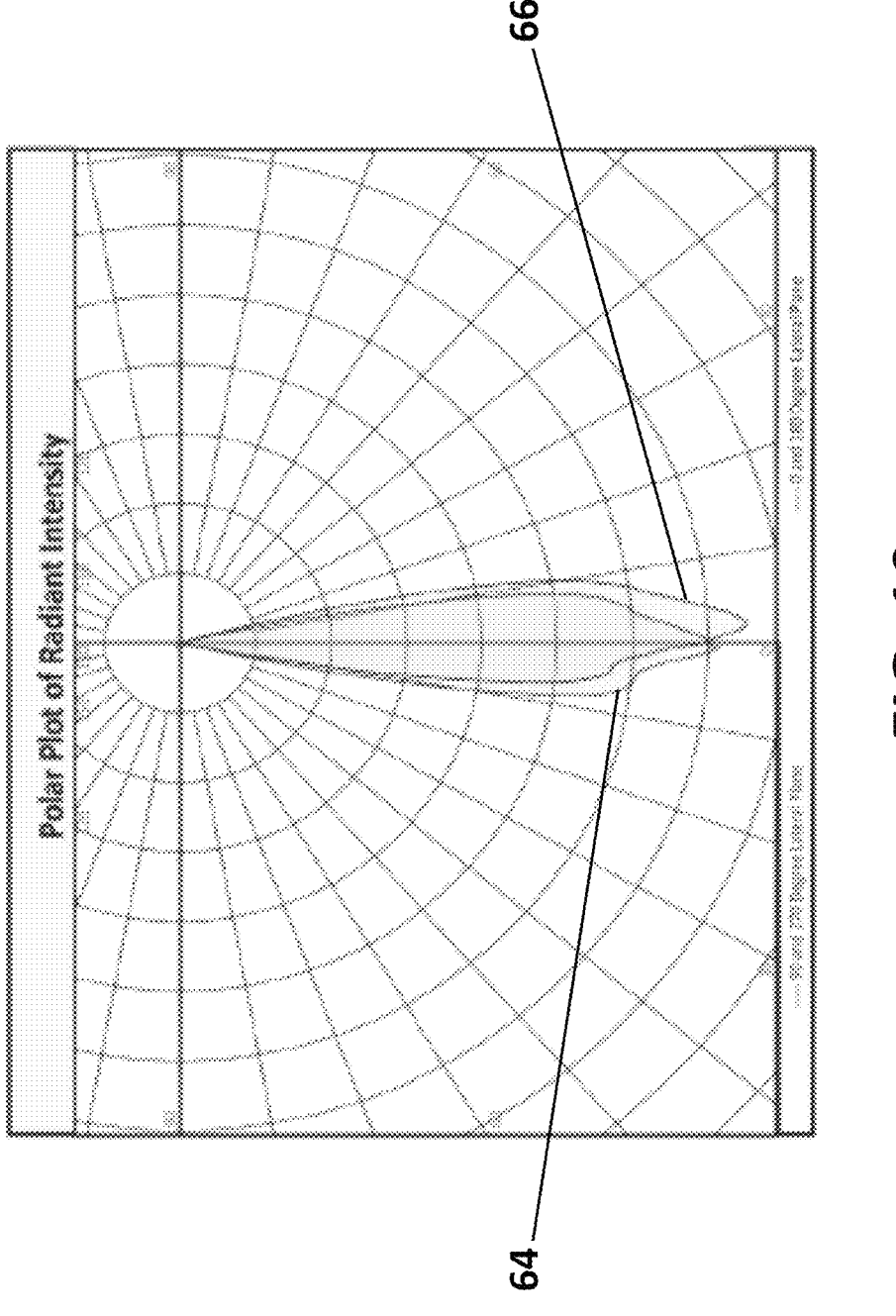
FIG. 10 is a polar plot of intensity (in relative units) versus angle (in degrees) showing the angular distribution of light output by the UVC light source comprising a UVC LED and a lens. The UVC LED outputs light that diverges into a relatively wide angle up to 180 degrees (e.g., 120-180°) and the lens reduces the divergence angle of this light.

FIG. 10 shows the angular distribution of light output by the UVC light source 10. In particular, FIG. 10 is a polar plot of intensity (in relative units) versus angle (in degrees) showing the angular distribution of light output by the UVC light source 10 comprising the UVC LED 12 and the lens 16. As discussed above, the UVC LED 12 emits UVC light that diverges, for example, possibly as much as 120°, 1300 140°, 150°, 160°, 170°, or 1800 or any range formed by any of these values. The UVC light may diverge by other amounts as well. The lens 16, however, is configured to reduce the divergence. The lens 16 may, for example, reduce the divergence to 60°, 500 40°, 30°, 20°, 10°, 15°, 5°, 3°, or 1° or any value between any of these ranges. For example, the divergence may be between 400 and 5°, 400 and 10°, 400 and 15°, 300 and 5°, 300 and 10°, 300 and 15°, 200 and 5°, 200 and 10°, 200 and 15°, e.g., 18°. In some designs, most, if not all, the light or possibly at least 20%, 30%, 40%, 50%, 60%, 70%, 80%, 90%, 95%, 98%, 99%, or 100% of the light (or any range formed by any of these values) output by these UVC light sources 12 are directed forward and project light forward (e.g., mostly in the Z direction as shown by the XYZ coordinate system) or within an angular range of ±60°, ±50°, ±40°, ±30°, ±20°, ±10°, ±15°, ±5°, ±3°, or ±1° of the forward (Z) direction or any range formed by any of these values, or possibly larger or smaller. In some designs, the divergence angle and/or beam width varies with effective focal length. In various designs, the effective focal length may be, for example, 15 mm, 14 mm, 13 mm, 12 mm, 11 mm, 10 mm, 9 mm, 8 mm, 7 mm, 6 mm, 5 mm, 4 mm, 3 mm, 2 mm, or 1 mm or any range formed by any of these values. Focal lengths outside these ranges are also possible. Similarly, the distance from the UVC LED 14 and the lens 16 may be 15 mm, 14 mm, 13 mm, 12 mm, 11 mm, 10 mm, 9 mm, 8 mm, 7 mm, 6 mm, 5 mm, 4 mm, 3 mm, 2 mm, or 1 mm or any range formed by any of these values although other distances, for example, outside such ranges may be possible. In some designs, the distance between UVC LED 14 and the lens 16 may be the same although in other designs the distance is not identical.

The distributions 64, 66 in the 0 to 180° angular plane and the 90° to 270° angular plane, respectively, are shown. In the example shown, the divergence is estimated to be about 180 for a lens 16 having an effective focal length of 7.0 mm. The focal length may vary as may the divergence of the UVC light output by the lens 16.

As discussed above, in various designs, the UVC light source(s) 12 is configured to be oriented and/or is oriented so as to point along the length of the duct 50, for example, along the longitudinal direction (e.g., Z direction). The orientation of the UVC light source(s) 12, the UVC LED(s) 14, the lens(es) 16 (e.g., the optical axis(es) of the lens(es) or the optical system(s) combining the UVC LED(s) and the lens(es)) can be and/or can be configured to be, for example, within ±45°, ±40°, ±35°, ±30°, ±25°, ±20°, ±15°, ±10°, ±5°, ±4°, ±3°, ±2°, or ±1°, of the longitudinal direction (e.g., Z direction) and/or direction in which the length of the duct 50 extends or any range between any of these values.

Likewise, in various implementations, most (e.g., at least 55%, 60%, 65%, 70% 75%, 80%, 85%, 90%, 95%, 98%, 99% or any range between any of these values) of the UVC light emitted from the UVC light projection unit 10 and the UVC light source(s) 12 is oriented or can be configured to be to point more along the length of the duct 50, for example, along the longitudinal direction (e.g., Z direction) than in different directions. For example, the orientation of most of the emitted UVC light (e.g., at least 55%, 60%, 65%, 70% 75%, 80%, 85%, 90%, 95%, 98%, 99%,) and/or the UVC light source(s) 12 can be or can be configured to be within ±45°, ±40°, ±35°, ±30°, ±25°, ±20°, ±15°, ±10°, ±5°, ±4°, ±3°, ±2°, ±1°, of the longitudinal direct (e.g., Z direction) and/or direction in which the length of the duct 50 extends or any range between any of these percentages or angles. In various implementations, the UVC light is directed in the direction opposite to the flow of the air, however, in other implementations the UVC light can be directed along the direction of the flow of the air. The UVC light projection unit 10, e.g., the elongate support or arm 28, is designed to point the UVC light source(s) 12 and hence direct the UVC light into the oncoming air flow. In other implementations, the UVC light projection unit can be arranged to point the UVC light source(s) 12 and hence direct the UVC light into trailing the air flow or along the direction of the air flow.

As discussed above, as the air is flowing along the length of the duct or shaft, directing the UVC light along the length of the duct or shaft provides for a longer time over which a portion of the air is exposed to the UVC light, which can increase the effectiveness of the sterilization and/or inactivation process.

Accordingly, in various implementations, the UVC light source 10 is oriented or can be configured to be oriented to point in a direction parallel to the mounting platform 34 and/or to the bottom of the mounting platform and/or orthogonal to a normal to the mounting platform 34 and/or to the bottom of the mounting platform or within ±45°, ±40°, ±35°, ±30°, ±25°, ±20°, ±15°, ±10°, ±5°, ±4°, ±3°, ±2°, or ±1° or any range between any of these values. Likewise, in various implementations, the elongate support or arm 28 is oriented or can be configured to be oriented to point in a direction normal to the mounting platform 34 and/or to the bottom of the mounting platform or within ±45°, ±40°, ±35°, ±30°, ±25°, ±20°, ±15°, ±10°, ±5°, ±4°, ±3°, ±2°, or ±1° or any range between any of these values.

Other configuration of the UVC light projection unit 10 than shown in FIGS. 3-5 can be employed to direct UVC light along the direction of the length of the duct 50. FIG. 11, for example, illustrates a UVC light projection unit 10 having a different design.

The UVC light projection unit 10 includes a plurality of light sources 12, three in this example, although the number can be higher or lower. For example, the UVC light projection unit 10 may have a single light source 12 in some designs or may have two and only two light sources or three and only three light sources (as in the example shown in FIG. 11) in some implementations. The UVC light sources 12 are supported by an elongate support or support arm 28. The elongate support or arm 28 has a low profile to reduced air resistance. The elongate support or arm 28 may for example have a smaller thickness (e.g., in the y direction) than width (in the x direction) and depth (e.g., in the z-direction). The elongate support or arm 28 is supported by a frame 68. As discussed above, in various implementations, the elongate support or arm 28 has a shape to reduce air resistance. A front end of this elongate support or arm 28 that faces the air flow may, for example, have a curved profile and/or the thickness of the elongate support or arm 28 may be tapered at the opposite end or rear end. Accordingly, in some implementations, the elongate support or arm 28 is shaped like a wing. In some implementations, this elongate support or arm 28 is located at the center of the air duct or plenum and/or frame 68. In the example shown, the frame 68 has a circular shape (e.g., along a cross-section of the frame orthogonal to the length thereof and/or orthogonal to the length of the air duct) to fit within an air duct 50 having a circular cross-section (e.g., orthogonal to the length of the air duct). Other shapes such as square or rectangular may be used in other cases.

In various implementations the size of the fame is approximately the size of the air duct to fit therein. In various implementations, for example, the size, e.g., width, height, diameter, or any combination thereof, is approximately 6, 8, 10, 12, 14 inches or larger or any range between any of these values. Likewise, in various implementations, for example, the size, e.g., width, height, diameter, or any combination thereof, is from 5 to 7 inches, from 7 to 9 inches, from 9 to 11 inches, from 11 to 13 inches, from 13 to 15 inches or larger or any range formed by any of these values. Smaller or larger sized are possibly. In some implementations, the size and shape of the frame are sufficiently close to the size and shape of the duct (e.g., in the cross-section orthogonal to the longitudinal direct such as z direction and length of the duct) such that the frame fits snuggly and/or conformally into the duct. In some implementations, however, the frame is slightly smaller to fit within the duct. In some implementations, the frame is secured to the duct, for example by screws or other fasteners.

As discussed above in connection with FIGS. 1 and 2, the UVC light sources 12 (e.g., 12a, 12b, 12c) may comprise UVC LEDs 14 and lenses 16 optically transmissive to UVC light such as UVC light emitted by the LEDs. The UVC light sources 12 (e.g., 12a, 12b, 12c) may comprise an optics housing region or outer optics retaining housing 20 to which the LED 12 and/or lens 16 are attached. As illustrated, the UVC light sources 12 (e.g., 12a, 12b, 12c) also comprise heat dissipation fins 30. The UVC light sources 12 (e.g., 12a, 12b, 12c) may have other features such as other features of UVC light sources discussed herein. Still other configurations and variation are possible.

Another example is shown in FIGS. 12A-12D. FIG. 12A is a perspective view of the UVC light projection unit 10, similar to that shown in FIG. 5, having three light sources 12a, 12b, 12c. As discussed above, however, a larger or smaller number of light sources 12 may be included in the UVC light projection unit 10. Also shown is the mounting platform 34 and the elongate support or arm 28 on which the light sources 12a, 12b, 12c are mounted or supported.

FIG. 12B is an exploded perspective view of the UVC light projection unit 10 of FIG. 12A. FIG. 12B illustrates that in this design a single elongate support or arm 28 supports the plurality (e.g., 3) of light sources 12a, 12b, 12c. This elongate support or arm 28 may also support electrical wiring 70 such as for providing power to the UVC LEDs 14. The wiring 70 may be included in and/or on the elongate support or arm 28. Ends of wires 70 for connecting to respective UVC LEDs 14 are shown in FIG. 12B. Such wiring 70 may electrically connect electronics in the mounting platform or control box 34 to the UVC LEDs 14 in the respective UVC light sources 12a, 12b, 12c. As discussed above, more or less UVC light sources 12 may be included in the UVC light projection unit 10.

FIG. 12C is a perspective view one of the UVC light sources 12a, 12b, 12c in the design of FIGS. 12A and 12B showing the UVC LED 14 electrically connected to wires 70 that may be supported by the elongate support or arm 28. FIG. 12C also shows the UVC LED 14 mounted on a platform such as a printed circuit board (PCB) 27, which may be disposed on a heat sink 29, which may serve to transfer heat from the UVC LED to the heat dissipation fins 30. In some implementations, the heat sink 29 and fins 30 comprise a monolithic structure such as a monolithic metal structure although other designs are possible. Screws are shown securing the PCB, e.g., to the heat sink 27. In particular, PCB board is shown held in place by two small screws on opposing sides of the PCB in this example. As illustrated, the small PCB board is on the front center of the heatsink 29. The wires 70 come in from different sides and are soldered onto small terminals on opposite sides of the PCB board.

FIG. 12D is a cross-sectional view of the optics mount or retainer 20 and lens 16 for one of the UVC light sources 12a, 12b, 12c in the design of FIG. 12A-12C. FIG. 12D shows the UVC LED 14 and a channel 22 through which UVC light passes from the UVC LED to the lens 16. This optics mount or retainer 20 and/or the channel 22 may be configured to establish a suitable distance between the lens 16 and the UVC LED 14 to, for example, provide an appropriate amount of divergence and/or collimation of the UVC light exiting the light source 12. FIG. 12D also shows sloped reflective surfaces 26 forming sidewalls of the channel 22. Other shaped surfaces 26 are possible. Such surfaces 26 may assist in collecting light from the UVC LED 14 that diverges widely (e.g., 120°, 130°, 140°, 150°, 160°, 170°, 1800 or any range between any of these values) and reducing the divergence and/or collimating the UVC light using the lens 16. As discussed above, such sloping may provide for collection of UVC light from the UVC LED 14 at a wider angle and directing to the lens 16 such that the light can be transmitted by the lens into a smaller angle. Likewise, the angle of the sidewall (e.g., the slope thereof), together with possibly the focal length of the lens 16 and/or the distance between the lens and the UVC LED 14, may influence the divergence angle of light exiting the lens 16 and emitted from the UVC light source 12. Also shown are through holes 74 for retaining screws.

Variations are possible. For example, the number of light sources 12a, 12b, 12c may vary.

Still other configurations and variation are possible.

As discussed above, various designs of UVC light projection unit 10 described herein may be partially or fully effective at sterilization and/or inactivation of, for example, viruses and/or bacteria, in the air of an HVAC device such as an air duct or plenum device (e.g., air duct). In various implementations, the UVC light projection unit 10 is configured to emit UVC light of sufficient power to destroy or disable air borne bacteria and/or or viruses to which the UVC light is directed. In various implementation the UVC light source(s) 12 is configured to provide sufficient power and the lens 16 is configured to sufficiently reduce the divergence angle of light emitted by the UVC LED and/or collimate the UVC light to affect (e.g., partially or fully destroy and/or disable certain viruses and bacteria in the UVC LED (e.g., air duct, plenum device, plenum) 50 within 10 feet of the UVC light source(s) positioned within the HVAC device (e.g., air duct, plenum device, plenum) and pointed along the length of the HVAC device (e.g., air duct, plenum device, plenum), e.g., in the z-direction. However, in other implementations, the distance could be larger or smaller, e.g., 13 feet, 12 feet, 11 feet, 10 feet, 9 feet, 8 feet, 7 feet, 6 feet, 5 feet, 4 feet, 3 feet, 2 feet, or 1 feet or any range between any of these values or possibly larger or smaller.

As discussed above, various examples are presented and/or discussed herein, in the context of use with ducts such as air duct. However, such structures, methods, features, characteristic, etc. may be applicable to HVAC devices more generally and may, for example, be applicable to plenum devices and/or plenums and/or plenum chambers.

EXAMPLES

The following is a numbered list of example embodiments that are within the scope of this disclosure. The example embodiments that are listed should in no way be interpreted as limiting the scope of the embodiments. Various features of the example embodiments that are listed can be removed, added, or combined to form additional embodiments, which are part of this disclosure.

Part I

1. An HVAC UVC light projection unit for providing UVC illumination within an HVAC device having an inside and an outside and a width in a transverse direction and extending along a longitudinal direction to flow air inside said HVAC device along or opposite to said longitudinal direction, said HVAC UVC light projection unit comprising:

a mounting platform configured to mount on the outside of said HVAC device;

an elongate support extending transversely from said mounting platform such that when said mounting platform is mounted on the outside of said HVAC device, at least a portion of the elongate support is within the HVAC device; and at least one UVC light source supported on said elongate support, said at least one UVC light source comprising a UVC light emitting diode (LED) configured to emit light having a wavelength in the range of 250 to 280 nm and a respective lens transmissive to UVC light, wherein said lens is disposed to receive UVC light from said UVC LED and transmit said UVC light such that said light is directed into said HVAC device, wherein said UVC light source is configured to be oriented so as to direct UVC light along the longitudinal direction of said HVAC device.

2. The HVAC UVC light projection unit of Example 1, wherein said UV light source comprises an optics mount, said lens attached to said optics housing region.

3. The HVAC UVC light projection unit of 2, wherein said lens is at a forward end of said optics mount and said UVC LED is at a rearward end of said optics mount.

4. The HVAC UVC light projection unit of Examples 2 or 3, wherein said optics mount comprise aluminum.

5. The HVAC UVC light projection unit of any of Examples 2-4, wherein said optics mount includes a channel therein, said channel having forward and rearward ends, said lens at said forward end and said UVC LED at said rearward end of said channel such that UVC light from said UVC LED propagates to said forward end of said channel through said lens.

6. The HVAC UVC light projection unit of Example 5, wherein said channel has sidewalls and a least a portion of the light from said UVC LED reflects off said sidewalls and thereby propagates from said UVC LED to said lens.

7. The HVAC UVC light projection unit of any of the examples above, wherein said UVC light source is configured to output collimated UVC light.

8. The UVC light projection unit of any of the examples above, wherein said lens has positive optical power.

9. The HVAC UVC light projection unit of any of the examples above, wherein said lens has a focal length and is disposed a focal length from said UVC LED.

10. The HVAC UVC light projection unit of any of the examples above, wherein said lens comprises an aspheric lens comprising at least one aspheric surface configured to refract UVC light.

11. The HVAC UVC light projection unit of any of the examples above, wherein said lens comprises a fused silica lens.

12. The HVAC UVC light projection unit of any of the examples above, further comprising a heat sink comprising a plurality of fins extending in a plurality of transverse directions radially from said UVC light source.

13. The HVAC UVC light projection unit of any of the examples above, having a single UVC light source.

14. The HVAC UVC light projection unit of Example 13, wherein said single UVC light source outputs radiant flux in the range from 100 to 200 mW.

15. The HVAC UVC light projection unit of any of Examples 1-12, comprising two UVC light sources and no more than two UVC light sources, said two UVC light sources comprising a first UVC light source spaced apart from a second UVC light source in the transverse direction.

16. The HVAC UVC light projection unit of Example 15, wherein said first UVC light source is supported by said elongate support member and said second UVC light source is supported by another elongate support member connected to the first UVC light source.

17. The HVAC UVC light projection unit of Example 15, wherein said first and second UVC light sources are supported on said elongate support.

18. The HVAC UVC light projection unit of any of Examples 15-17, wherein said first and second UVC light sources together output radiant flux in the range from 100 to 200 mW.

19. The HVAC UVC light projection unit of any of Examples 1-12, comprising three UVC light sources and no more than three UVC light sources, said three UVC light sources comprising a first UVC light source spaced apart from a second UVC light source in the transverse direction and a third UVC light source spaced apart from said first and second UVC light sources in the transverse direction.

20. The HVAC UVC light projection unit of Example 19, wherein said first UVC light source is supported by said elongate support member, said second UVC light source is supported by another elongate support member connected to the first UVC light source.

21. The HVAC UVC light projection unit of Example 20, wherein said third UVC light source is supported by another elongate support member connected to the second UVC light source.

22. The HVAC UVC light projection unit of Example 19, wherein said first, second, and third UVC light source are supported on said elongate support.

23. The HVAC UVC light projection unit of any of Examples 19-22, wherein said first, second, and third light sources together output radiant flux in the range from 180 to 250 mW.

24. The HVAC UVC light projection unit of any of the examples above, wherein said mounting platform include electronics for driving said UVC LED.

25. The HVAC UVC light projection unit of any of the examples above, wherein said mounting platform include a housing with said electronics inside and portions with through holes for screwing the mounting platform into said HVAC device.

26. The HVAC UVC light projection unit of any of Examples 1-24, further comprising portions with through holes for screwing the mounting platform into said HVAC device.

27. The HVAC UVC light projection unit of any of Examples 1-24, wherein a portion of the elongate support or a portion of the mounting platform or both extend into or through a hole in the HVAC device.

28. The HVAC UVC light projection unit of any of the examples above, wherein said UVC light emitting diode (LED) is configured to emit brightest in a wavelength in the range of 260 to 280 nm.

29. The HVAC UVC light projection unit of any of the examples above, further comprising said HVAC device with said mounting platform mounted on the outside of said HVAC device, wherein said HVAC device includes an hole therein, said elongate support connected to said mounting platform such that when said mounting platform is mounted on the outside of said HVAC device said at least one UVC light source is inside said HVAC device and oriented to direct UVC light along the longitudinal direction of the HVAC device.

30. The HVAC UVC light projection unit of Example 29, further comprising screws securing said mounting platform to said HVAC device.

31. The HVAC UVC light projection unit of any of the examples above, wherein said HVAC device comprises an air duct.

32. The HVAC UVC light projection unit of any of Examples 1-30, wherein said HVAC device comprises a plenum, plenum chamber, or plenum device.

33. The HVAC UVC light projection unit of any of the examples above, wherein said at least one UCV light source is configured to be oriented such that UVC light from said at least one UVC light source is directed opposite to said flow of air in said HVAC device.

34. The HVAC UVC light projection unit of any of the examples above, wherein said at least one UCV light source is oriented such that UVC light from said at least one UVC light source is directed opposite to said flow of air in said HVAC device.

35. The HVAC UVC light projection unit of any of the above, wherein said lens comprises fused silica having an internal transmittance corrected to eliminate the effects of scattering, absorption and surface reflection of UVC light with 245-280 nm wavelength of at least 90% for fused silica glass having a thickness of 10 mm.

36. The HVAC UVC light projection unit of any of the above, wherein said lens comprises fused silica having an internal transmittance corrected to eliminate the effects of scattering, absorption and surface reflection of UVC light with 245-280 nm wavelength of at least 95% for fused silica glass having a thickness of 10 mm.

37. The HVAC UVC light projection unit of any of the above, wherein said lens comprises fused silica wherein the OH content is not larger than 5 ppm.

38. The HVAC UVC light projection unit of any of the above, wherein said lens comprises fused silica wherein the content of each of Li, Na, K, Mg, Ca and Cu are smaller than 0.1 ppm.

39. The HVAC UVC light projection unit of any of the above, wherein said lens comprises fused silica fabricated by crystobalitizing powdery silica raw material and fusing the crystobalitized silica material in a non-reducing atmosphere.

Part II

1. An HVAC UVC light projection unit for providing UVC illumination within an HVAC device having an inside and an outside and a width in a transverse direction and extending along a longitudinal direction to flow air inside said HVAC device along or opposite to said longitudinal direction, said HVAC UVC light projection unit comprising:

a frame configured to be inserted inside the HVAC device;

an elongate support extending transversely with respect to the frame such that when said frame is in the inside of said HVAC device, the elongate support is within the HVAC device, said elongate support being supported by the frame; and at least one UVC light source supported on said elongate support, said at least one UVC light source comprising a UVC light emitting diode (LED) configured to emit light having a wavelength in the range of 250 to 280 nm and a respective lens transmissive to UVC light, wherein said lens is disposed to receive UVC light from said UVC LED and transmit said UVC light such that said light is directed into said HVAC device, wherein said UVC light source is configured to be oriented so as to direct UVC light along the longitudinal direction of said HVAC device.

2. The HVAC UVC light projection unit of Example 1, wherein said UV light source comprises an optics mount, said lens attached to said optics housing region.

3. The HVAC UVC light projection unit of Example 2, wherein said lens is at a forward end of said optics mount and said UVC LED is at a rearward end of said optics mount.

4. The HVAC UVC light projection unit of Example 2 or 3, wherein said optics mount comprise aluminum.

5. The HVAC UVC light projection unit of any of Examples 2-4, wherein said optics mount includes a channel therein, said channel having forward and rearward ends, said lens at said forward end and said UVC LED at said rearward end of said channel such that UVC light from said UVC LED propagates to said forward end of said channel through said lens.

6. The HVAC UVC light projection unit of Example 5, wherein said channel has sidewalls and a least a portion of the light from said UVC LED reflects off said sidewalls and thereby propagates from said UVC LED to said lens.

7. The HVAC UVC light projection unit of any of the examples above, wherein said UVC light source is configured to output collimated UVC light.

8. The UVC light projection unit of any of the examples above, wherein said lens has positive optical power.

9. The HVAC UVC light projection unit of any of the examples above, wherein said lens has a focal length and is disposed a focal length from said UVC LED.

10. The HVAC UVC light projection unit of any of the examples above, wherein said lens comprises an aspheric lens comprising at least one aspheric surface configured to refract UVC light.

11. The HVAC UVC light projection unit of any of the examples above, wherein said lens comprises a fused silica lens.

12. The HVAC UVC light projection unit of any of the examples above, further comprising a heat sink comprising a plurality of fins extending in a plurality of transverse directions radially from said UVC light source.

13. The HVAC UVC light projection unit of any of the examples above, having a single UVC light source.

14. The HVAC UVC light projection unit of Example 13, wherein said single UVC light source outputs radiant flux in the range from 100 to 200 mW.

15. The HVAC UVC light projection unit of any of Examples 1-12, comprising two UVC light sources and no more than two UVC light sources, said two UVC light sources comprising a first UVC light source spaced apart from a second UVC light source in the transverse direction.

16. The HVAC UVC light projection unit of Example 15, wherein said first UVC light source is supported by said elongate support member and said second UVC light source is supported by another elongate support member.

17. The HVAC UVC light projection unit of Example 15, wherein said first and second UVC light sources are supported on said elongate support.

18. The HVAC UVC light projection unit of Examples 15-17, wherein said first and second UVC light sources together output radiant flux in the range from 100 to 200 mW.

19. The HVAC UVC light projection unit of any of Examples 1-12, comprising three UVC light sources and no more than three UVC light sources, said three UVC light sources comprising a first UVC light source spaced apart from a second UVC light source in the transverse direction and a third UVC light source spaced apart from said first and second UVC light sources in the transverse direction.

20. The HVAC UVC light projection unit of Example 19, wherein said first UVC light source is supported by said elongate support member, said second UVC light source is supported by another elongate support member.

21. The HVAC UVC light projection unit of Example 20, wherein said third UVC light source is supported by another elongate support member.

22. The HVAC UVC light projection unit of Example 19, wherein said first, second, and third UVC light source are supported on said elongate support.

23. The HVAC UVC light projection unit of any of Examples 19-22, wherein said first, second, and third light sources together output radiant flux in the range from 180 to 250 mW.

24. The HVAC UVC light projection unit of any the examples above, wherein said UVC light emitting diode (LED) is configured to emit brightest in a wavelength in the range of 260 to 280 nm.

25. The HVAC UVC light projection unit of any of the examples above, wherein said frame has a shape the same as a cross-section of the HVAC device orthogonal to the length thereof.

26. The HVAC UVC light projection unit of any of the examples above, wherein said frame has a circular shape.

27. The HVAC UVC light projection unit of any of the examples above, further comprising said HVAC device with said frame included therein, said elongate support connected to said frame such that when said frame is in said HVAC device said at least one UVC light source is inside said HVAC device and oriented to direct UVC light along the longitudinal direction of the HVAC device.

28. The HVAC UVC light projection unit of any of the examples above, wherein said HVAC device comprises an air duct.

29. The HVAC UVC light projection unit of any of Examples 1-27, wherein said HVAC device comprises a plenum, plenum chamber, or plenum device.

30. The HVAC UVC light projection unit of any of the examples above, wherein said at least one UCV light source is configured to be oriented such that UVC light from said at least one UVC light source is directed opposite to said flow of air in said HVAC device.

31. The HVAC UVC light projection unit of any of the examples above, wherein said at least one UCV light source is oriented such that UVC light from said at least one UVC light source is directed opposite to said flow of air in said HVAC device.

32. The HVAC UVC light projection unit of any of the above, wherein said lens comprises fused silica having an internal transmittance corrected to eliminate the effects of scattering, absorption and surface reflection of UVC light with 245-280 nm wavelength of at least 90% for fused silica glass having a thickness of 10 mm.

33. The HVAC UVC light projection unit of any of the above, wherein said lens comprises fused silica having an internal transmittance corrected to eliminate the effects of scattering, absorption and surface reflection of UVC light with 245-280 nm wavelength of at least 95% for fused silica glass having a thickness of 10 mm 34. The HVAC UVC light projection unit of any of the above, wherein said lens comprises fused silica wherein the OH content is not larger than 5 ppm.

35. The HVAC UVC light projection unit of any of the above, wherein said lens comprises fused silica wherein the content of each of Li, Na, K, Mg, Ca and Cu are smaller than 0.1 ppm.

36. The HVAC UVC light projection unit of any of the above, wherein said lens comprises fused silica fabricated by crystobalitizing powdery silica raw material and fusing the crystobalitized silica material in a non-reducing atmosphere.

37. The HVAC UVC light projection unit of any of the examples above, wherein said plurality of UVC LEDs output light having a radiant flux in the range of from 200 to 400 mW.

38. The HVAC UVC light projection unit of any of the examples above, wherein said UVC light projection unit emits sufficient radiation to kill or disable most of the bacteria and/or viruses on a surface that is 6 inches from the UVC light projection unit within 15 seconds.

39. The HVAC UVC light projection unit of any of the examples above, wherein said UVC light projection unit emits sufficient radiation to kill or disable most of the bacteria and/or viruses on a surface that is 1 foot from the UVC light projection unit within 15 seconds.

40. The UVC HVAC light projection unit of any of the examples above, wherein said UVC light projection unit comprises a lithium phosphate rechargeable power system powered by a lithium phosphate rechargeable battery.

Part III

1. A method of installing an HVAC UVC light projection unit for providing UVC illumination within an HVAC device having an inside and an outside and a width in a transverse direction and extending along a longitudinal direction to flow air inside said HVAC device along or opposite to said longitudinal direction, said method comprising:

providing said HVAC UVC light projection unit comprising:

a mounting platform configured to mount on the outside of said HVAC device;

an elongate support extending transversely from said mounting platform; and at least one UVC light source supported on said elongate support, said at least one UVC light source comprising a UVC light emitting diode (LED) configured to emit light having a wavelength in the range of 250 to 280 nm, inserting said an elongate support and said at least one UVC light source into said HVAC device through a hole in said HVAC device; and mounting said mounting platform on the outside of said HVAC device.

2. The method of Example 1, further comprising cutting said hole in a wall of said HVAC device.

3. The method of Example 1 or 2, further comprising orienting said at least one UCV light source such that UVC light from said at least one UVC light source is directed along the longitudinal direction of said HVAC device.

4. The method of any of the examples above, further comprising orienting the mounting platform when said mounting platform on the outside of said HVAC device such that UVC light from said at least one UVC light source is directed along the longitudinal direction of said HVAC device.

5. The method of any of the examples above, further comprising orienting said at least one UVC light source such that UVC light from said at least one UVC light source is directed opposite to said flow of air in said HVAC device.

6. The method of any of the examples above, further comprising orienting the mounting platform when said mounting platform on the outside of said HVAC device such that UVC light from said at least one UVC light source is directed opposite to the flow of air in said HVAC device.

7. The method of any of the examples above, further comprising screwing said mounting platform to said HVAC device.

8. The method of any of the examples above, wherein said HVAC device comprises an air duct.

9. The method of any of Examples 1-7, wherein said HVAC device comprises a plenum, plenum chamber, or plenum device.

A wide range of variations are possible. Structures, components, and/or feature, for example, can be added, removed, and/or rearranged.

Conclusion

Various embodiments of the present invention have been described herein. Although this invention has been described with reference to these specific embodiments, the descriptions are intended to be illustrative of the invention and are not intended to be limiting. Various modifications and applications may occur to those skilled in the art without departing from the true spirit and scope of the invention.

What is claimed is:

1. An HVAC UVC light projection unit for providing UVC illumination within an HVAC device having an inside and an outside and a width in a transverse direction and extending along a longitudinal direction to flow air inside said HVAC device along or opposite to said longitudinal direction, said HVAC UVC light projection unit comprising:

a mounting platform configured to mount on the outside of said HVAC device;

an elongate support extending transversely from said mounting platform such that when said mounting platform is mounted on the outside of said HVAC device, at least a portion of the elongate support is within the HVAC device, said elongate support having a smaller thickness that faces the airflow than width in a transverse direction or depth in the longitudinal direction;

at least one UVC light source supported on said elongate support, said at least one UVC light source comprising a UVC light emitting diode (LED) configured to emit light and a respective lens transmissive to UVC light, more than 90% of the light emitted from the UVC LED being in the UVC wavelength range of from 250 to 280 nm, wherein said lens is disposed to receive UVC light from said UVC LED and transmit said UVC light such that said light is directed into said HVAC device, wherein said at least one UVC light source is configured to be oriented so as to direct the majority of the UVC light along the longitudinal direction of said HVAC device; and at least one heat sink comprising a plurality of fins extending in a plurality of transverse directions radially from said UVC light source, said fins having a thickness that is smaller than their depth in the longitudinal direction and width in the transverse direction, said thickness of the fins facing the airflow, both the depth of said fins and the depth of said elongate support extending in the same direction, said width of said fins shorter than the width of said elongate support, wherein said at least one UVC light source comprises a plurality of light sources and said at least one heat sink comprises a plurality of heat sinks, different fins for different heat sinks surrounding different light sources, and wherein said at least one UVC light source is configured to be oriented such that the majority of the UVC light from said at least one UVC light source is directed opposite to said flow of air in said HVAC device such that the UVC light is directed into the oncoming airflow.

2. The HVAC UVC light projection unit of claim 1, wherein said at least one UVC light source comprises an optics mount, said lens attached to an optics housing region.

3. The HVAC UVC light projection unit of claim 2, wherein said lens is at a forward end of said optics mount and said UVC LED is at a rearward end of said optics mount.

4. The HVAC UVC light projection unit of claim 2, wherein said optics mount comprise aluminum.

5. The HVAC UVC light projection unit of claim 2, wherein said optics mount includes a channel therein, said channel having forward and rearward ends, said lens at said forward end and said UVC LED at said rearward end of said channel such that UVC light from said UVC LED propagates to said forward end of said channel through said lens.

6. The HVAC UVC light projection unit of claim 1, wherein said UVC light source is configured to output collimated UVC light.

7. The HVAC UVC light projection unit of claim 1, wherein said lens comprises an aspheric lens comprising at least one aspheric surface configured to refract UVC light.

8. The HVAC UVC light projection unit of claim 1, wherein said lens comprises a fused silica lens.

9. The HVAC UVC light projection unit of claim 1, wherein said mounting platform includes electronics for driving said UVC LED.

10. The HVAC UVC light projection unit of claim 9, wherein said mounting platform includes a housing with said electronics inside and portions with through holes for screwing the mounting platform into said HVAC device.

11. The HVAC UVC light projection unit of claim 1, wherein said HVAC device comprises an air duct.

12. The HVAC UVC light projection unit of claim 1, wherein said HVAC device comprises a plenum, plenum chamber, or plenum device.

13. The HVAC UVC light projection unit of claim 1, wherein said UVC light emitting diode (LED) is configured to emit brightest in a wavelength in the range of 260 to 280 nm.

14. The HVAC UVC light projection unit of claim 1, wherein said UVC light projection unit emits sufficient radiation to kill or disable most of the bacteria and/or viruses on a surface that is 1 foot from the UVC light projection unit within 15 seconds.

15. The HVAC UVC light projection unit of claim 1, wherein the orientation of said UVC light source is within ±20° of the direction in which the length of the duct extends such that most of the UVC light is directed along the length of the duct.

16. The HVAC UVC light projection unit of claim 1, wherein the orientation of most of the emitted UVC light is within ±20° of the longitudinal direction or direction in which the length of the duct extends.

17. The HVAC UVC light projection unit of claim 1, wherein said lens or the UVC LED and said lens has an optical axis within ±20° of the longitudinal direction or direction in which the length of the duct extends.

* * * * *